(12) United States Patent
Akita et al.

(10) Patent No.: US 11,098,288 B2
(45) Date of Patent: Aug. 24, 2021

(54) D-TYPE AMINO ACID DEHYDROGENASE

(71) Applicants: Kureha Corporation, Tokyo (JP); National Institute Of Advanced Industrial Science And Technology, Tokyo (JP)

(72) Inventors: Hironaga Akita, Higashi-hiroshima (JP); Yuusuke Nakamichi, Higashi-hiroshima (JP); Masahiro Watanabe, Higashi-hiroshima (JP); Akinori Matsushika, Higashi-hiroshima (JP); Tomotake Morita, Tsukuba (JP)

(73) Assignees: KUREHA CORPORATION, Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/637,444

(22) PCT Filed: Aug. 9, 2018

(86) PCT No.: PCT/JP2018/029889
§ 371 (c)(1),
(2) Date: Feb. 7, 2020

(87) PCT Pub. No.: WO2019/031574
PCT Pub. Date: Feb. 14, 2019

(65) Prior Publication Data
US 2020/0248153 A1    Aug. 6, 2020

(30) Foreign Application Priority Data
Aug. 9, 2017    (JP) ............................. JP2017-154621

(51) Int. Cl.
| | | |
|---|---|---|
| C12N 9/10 | (2006.01) | |
| C12N 9/02 | (2006.01) | |
| C12P 13/04 | (2006.01) | |
| C12N 15/00 | (2006.01) | |
| C12N 9/06 | (2006.01) | |
| C12N 15/52 | (2006.01) | |
| C12N 5/10 | (2006.01) | |

(52) U.S. Cl.
CPC ........... *C12N 9/0016* (2013.01); *C12N 15/52* (2013.01); *C12P 13/04* (2013.01); *C12N 5/10* (2013.01); *C12Y 206/01* (2013.01)

(58) Field of Classification Search
CPC ........... C12P 13/04; C12N 9/90; C12N 15/09; C12N 15/63; C12N 15/70; C12N 9/0016; C12Y 104/01; C12Y 104/01018; C12Y 206/01
USPC .......... 435/108, 106, 128, 191, 463
See application file for complete search history.

(56) References Cited

FOREIGN PATENT DOCUMENTS

JP    2017-108740 A    6/2017

OTHER PUBLICATIONS

"UniProtKB—A0A1M5M5H3 : Meso-diaminopimelate D-dehydrogenase," UniProtKB, dated Mar. 15, 2017, retrieved from the Internet <URL: http://ibis.internal.epo.org/exam/dbfetch.jsp?id=UNIPROT:A0A1M5M5H3> on Apr. 24, 2020, p. 1 of 1.
Gao, X. et al., "A Novel meso-Diaminopimelate Dehydrogenase from Symbiobacterium thermophilum: Overexpression, Characterization, and Potential for d-Amino Acid Synthesis," Applied and Environmental Microbiology, Dec. 1, 2012, vol. 78, No. 24, DOI: 10.1128/AEM.02234-12, pp. 8595-8600.
Liu, W. et al., "Structural and Mutational Studies on the Unusual Substrate Specificity of meso-Diaminopimelate Dehydrogenase from Symbiobacterium thermophilum," CHEMBIOCHEM, first published on Dec. 11, 2013, vol. 15, No. 2, DOI: 10.1002/cbic.201300691, pp. 217-222.
Gao, X. et al., "Engineering the meso-Diaminopimelate Dehydrogenase from Symbiobacterium Thermophilum by Site Saturation Mutagenesis for D-phenylalanine Synthesis," Applied and Environmental Microbiology, Aug. 15, 2013, vol. 79, No. 16, DOI: 10.1128/AEM.01049-13, pp. 5078-5081.
Akita, H. et al., "Highly stable meso-diaminopimelate dehydrogenase from an Ureibacillus thermosphaericus strain A1 isolated from a Japanese compost: purification, characterization and sequencing," AMB Express, published: Nov. 25, 2011, vol. 1, Article No. 43, DOI: 10.1186/2191-0855-1-43, pp. 1-8.
Extended European Search Report issued by European Patent Office Patent Application No. EP18844724.7 with search date of Apr. 30, 2020.
Notification of Reasons for Refusal First Office Action issued by the Japanese Patent Office for Japanese Patent Application 2019-535714 dated Jan. 21, 2020.
Translation of the Notification of Reasons for Refusal First Office Action issued by the Japanese Patent Office for Japanese Patent Application 2019-535714 dated Jan. 21, 2020.
GenBank Database [online], Accession No. FQWY01000010.1, dated Dec. 2, 2016, retrieved from Internet URL< https://www.ncbi.nlm.nih.gov/nuccore/FQWY01000010>, pp. 1-26.
Akita, H. et al., "Thermostable artificial NADP+-dependent D-amino acid dehydrogenase: its creation and application," Vitamins (Japan) 2016, vol. 90 (11), pp. 544-554.

(Continued)

*Primary Examiner* — Robert B Mondesi
*Assistant Examiner* — Mohammad Y Meah
(74) *Attorney, Agent, or Firm* — Abel Schillinger, LLP

(57) ABSTRACT

An enzyme having the following characteristics (a) and (b):
(a) the enzyme has an activity of reversible dehydrogenation of D-amino acids;
(b) the enzyme is a hexamer of polypeptides having an amino acid sequence having 80% or greater identity to the amino acid sequence of SEQ ID NO: 2.

8 Claims, 6 Drawing Sheets
Specification includes a Sequence Listing.

(56) References Cited

OTHER PUBLICATIONS

Akita, H. et al., "Creation of a thermostable NADP+-dependent D-amino acid dehydrogenase from Ureibacillus thermosphaericus strain A1 meso-diaminopimelate dehydrogenase by site-directed mutagenesis," Biotechnol Lett., published online May 22, 2012, vol. 34, pp. 1693-1699.
International Search Report of the International Searching Authority for PCT/JP2018/029889 dated Oct. 23, 2018.
English translation of International Search Report of the International Searching Authority for PCT/JP2018/029889 dated Oct. 23, 2018.
Written Opinion of the International Preliminary Examining Authority of PCT/JP2018/029889 dated Oct. 23, 2018.
English translation of Written Opinion of the International Preliminary Examining Authority of PCT/JP2018/029889 dated Oct. 23, 2018.
Office Action from European Patent Application No. 18844724.7 dated Oct. 19, 2020, 4 pages.
Office Action issued in the EP Patent Application No. 18844724.7, dated Feb. 5, 2021, 3 pages.

CATATGGGCGAAAAGATAAGAGTAGCTATTGTGGGTTATGGCAATATAGGAAGATATGCTTTAGATGCTATAA
AGGCAGCTCCTGATATGGAATTAGCCCGGGGTAGTTCGCAGGTCTTCATCTCTGGGGGATAAGCCGGCAGAACT
GGCTGATGTGCCGGTAGTAGGGTCTATTAAGGAACTTACAGGGGTAAAGGTAGCCCTTTTATGTACCCCTACC
CGTTCAGTACCGGAGTATGCCAGAGAGATTTAGCTCTTGGCATTAATACGGTTGACAGTTATGATATTCATG
GCCAGTTAGCTGATTTACGATTGGAATTAGATAAAGTTGCCAAGGAACATAATGCAGTAGCGGTGATATCAGC
CGGCTGGGATCCGGGAACTGATTCCATGGTGCGCTGTATGTTTGAATTTATGGCTCCCAAAGGTATAACCTAC
ACCAATTTTGGCCCCGGCATGAGCATGGGGCACTCGGTAGCCGTAAAGGCGGTTAAAGGGGTTAAAAATGCCC
TTTCTATGACTATACCTTTAGGCACCGGTGTGCATCGGCGCATGGTTTATGTGGAATTAGAACCGGGAGCTGA
TTTTGCCCAGGTAGAAAAGGCAGTAAAAACTGATCCCTATTTTGTAAAAGATGAAACTCATGTCATCCAGGTA
GAAGATGTTGATGCCCTTATCGATATGGGACATGGAGTATTGATGGAAAGAAAAGGAGTATCTGGCGGTACCC
ACAATCAGTTGTTAAGTTTTTCCATGCGCATAAACAATCCGGCTTTAACTGCTCAGATAATGGTAGCTTCGGC
CAGAGCCAGTGTAAAACAGAAACCTGGTGCTTATACTATGATTCAGATACCGATAATAGACTATATGTATGGA
GATCCTGACGAAATTATCCGCCAGCTTGTATAACTCGAG (SEQ ID NO: 1)

FIG. 1

MGEKIRVAIVGYGNIGRYALDAIKAAPDMELAGVVRRSSSLGDKPAELADVPVVGSIKELTGVKVALLCTPTR
SVPEYAREILALGINTVDSYDIHGQLADLRLELDKVAKEHNAVAVISAGWDPGTDSMVRCMFEFMAPKGITYT
NFGPGMSMGHSVAVKAVKGVKNALSMTIPLGTGVHRRMVYVELEPGADFAQVEKAVKTDPYFVKDETHVIQVE
DVDALIDMGHGVLMERKGVSGGTHNQLLSFSMRINNPALTAQIMVASARASVKQKPGAYTMIQIPIIDYMYGD
PDEIIRQLV (SEQ ID NO: 2)

FIG. 2

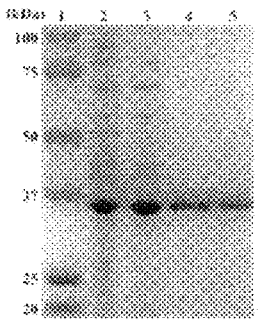

FIG. 3

FIG. 4

```
B. sphaericus     1 -MSALRVGIVGYGNLGRGVEFAISQNPDMELVAVFTRRDPNSTVSYASNASVYLVDDALKF  59
C. glutamicum     1 -MTNIRVAIVGYGNLGRSVEKLIAKQPDMELVGIFSRKATL----GTKIPVEDVADVQKH  55
S. thermophilum   1 -MDKLRVAVVGYGNVGRYALIAVQAAPDMELVGVVERKV-LAATPYELIGVRVVIDI-SQ  57
Y. lipolytica     1 MSEKIRVAIVGYGNLGRYALDAIKAAPDMELAGVVRRSLSLGDAPAELADVPVVGSL-RE  59
U. thermosphaericus 1 -MSKIRIGIVGYGNLGPGVEAAIQDNPDMELVANFTRDPKTVAYKSNVKVLHVEDAQSY  59
                      .* *:******.**:   :* * ::****.*        *  :*:*:

B. sphaericus    60 QRDIDVMILCGGSATDLPEQGPHFAQWFNTIDSFDTHAKIPLFFDAVDAAAQKSGKVSVI 119
C. glutamicum    56 ADVDVLFLQKGSATDIPQAPKFAQFACTVDTYDNHRDIPDRKQNWDEAATAAQSVALV 115
S. thermophilum  58 LEGVQGALLCVPTRSVPEYAEAMLRRCINTVDSYDIHGRLAQLRRRLDPVARLHGAAAVI 117
Y. lipolytica    60 LTGVRVALLCTPTRSVPEYAREILACGINTVDSYDIHHQLAQKRLELDPVARLHSAVAVI 119
U. thermosphaericus 60 KDELDVMILCGGSATDLPEQGPYFAQYFNTIDSFDTHABIPDYFDAVNAAALQSGKVAII 119
                         * ::      **:  *    .           :.          :      .:.::

B. sphaericus   120 SVGWDPGLFSLNRVLGEAVLPVGTTYTFWGDELSQGHSDAVRRITGVKNAVQYTLPIKDA 179
C. glutamicum   116 STGWDPGMFSINRVYAAAVLAERQGMFFRGPGLSQGHSDALRRIPGVQRAVQYTLPSEDA 175
S. thermophilum 118 SAGWDPGTDSIIRALLERNAPKGITYTNFGPGMSNGHSVAVRAAIPGVRDALSMIIPAQM-  176
Y. lipolytica   120 SAGWDPGTDSMVRKMFEPMAPKGITYTNFGPGMSNGHSVAVKAVKGVKNALSMTIPLGT-  178
U. thermosphaericus 120 SVGWDPGLFSLNRLLGEVVLPVGNTYTFWGKGVSQGHSDAIRRIQGVKNAVQYTIPIREA 179
                        *.*****   :::   :        *:  * ::*:*:: *   * *::*   :

B. sphaericus   180 VERMNREGENPELTTREKHARECSVVLEGGADAPKVEQEIVTMPDYFDGYNTTYNFISELE 239
C. glutamicum   176 LEKANSREAGDLTGKQTHKRQEFVVAD-AAQHERIEMDIRTMPDYFVGYLVEVYNFIRLAT 234
S. thermophilum 177 ------------GVNKRANYVELLEPGADFAEVERSAIKTDPYFV-RDETRVYQV---E  217
Y. lipolytica   179 ------------GVNKRMVYVELLEPGADFAQVEKAVKTDPYFV-SDLTRVIQV---E  219
U. thermosphaericus 180 VNRVSGERPELSTREKHAREICFVVLEGGADAFKVEHEIKTMPDYFDGYDITYHFISEEE 239
                                      *  *        :***  .***  * :  ***:*:  :        :

B. sphaericus   240 FNANWTGHPHGGIVIRSGESGANCHKQILFFSLKLESNPNFTSSVLVAYAAARELSQAGE 299
C. glutamicum   235 FDSKHTQMMPGGHVITTGDTGG-FNRTVEYILKLDRNPQFTASSQLAFGRAAHEWKRQCQ 293
S. thermophilum 218 SVSALNDVGRGVNNRKGVSGATHNQLFRFEMRINNPALTRDMVMAAIRAAARK---QK 272
Y. lipolytica   220 DVDALIDNGKVLNERGVSGGTHNQLLSFMKIENNPALTAQDMVACANASVK---QK 274
U. thermosphaericus 240 LKQNHSGHPHGGFVIRSGKSDGFGHKQIIERSLNLESNPMFTSSALVAYARAYRL SNGQ 299

B. sphaericus   300 RGAKTVEDIPTGLLSPKSAQLRKLLI 326
C. glutamicum   294 SGAFTVLEVAPTLLSPNKDRLIARNW 320
S. thermophilum 273 PGCYTMLEIPVLDYLPGQREANTRELV 299
Y. lipolytica   275 PGAYTMIQIPLLDMYGQPRELIRGLV  301
U. thermosphaericus 300 KGAKTVFDIPFQLLSPKSPFDLRKLLI 326
                      *:  ::::    .  :
```

FIG. 11

ATGGGTGAGAAGATTCGCGTGGCAATTGTTGGCTACGGCAATATCGGCCGCTACGCTTTAGATGCCAT
TAAAGCCGCCCCGGATATGGAACTGGCCGGTGTTGTGCGTCGTAGCAGCTCTTTAGGCGATAAACCGG
CAGAACTGGCCGATGTGCCGGTGGTGGGCAGCATCAAAGAGCTGACCGGTGTGAAAGTGGCTTTATTA
TGTACACCGACCCGCAGTGTGCCGGAGTATGCCCGTGAAATTCTGGCTTTAGGCATTAATACCGTGGA
TAGCTATTCTATTCACGGCCAGCTGGCAGATTTACGTTTAGAACTGGATAAAGTGGCCAAGGAGCACA
ATGCAGTGGCCGTGATTAGCGCTGGTTGGGATCCGGGTACCGATAGCATGGTGCGTTGCATGTTCGAG
TTTATGGCCCCGAAAGGCATTACCTACACCAATTTCGGCCCGGGTATGTCTTTAGGTCATAGTGGTGC
CGTGAAAGCCGTGAAAGGCGTGAAGAACGCTTTAAGCATGATTATCCCGCTGGGTACCGGCGTTCACC
GCATGATGGTGTATGTGGAACTGGAACCGGGTGCCGATTTTGCCCAAGTTGAAAAAGCCGTGAAGACC
GATCCGTACTTCGTGAAGGACGAGACCCACGTGATTCAAGTTGAGGATGTGGATGCTTTAATCGATAT
GGGTAACGGCGTGCTGATGGAACGTAAAGGCGTGAGCGGCGGCACCCATAACCAGCTGCTGAGCTTTA
GCATGCGCATCAACAACCCCGCTCTGACCGCCCAGATTATGGTGGCCAGTGCCCGTGCCAGCGTGAAA
CAGAAACCGGGTGCCTACACCATGATCCAGATCCCGATCATTGACTATATGTATGGCGATCCGGATGA
AATCATCCGCCAACTGGTTTAA (SEQ ID NO: 7)

FIG. 12

MGEKIRVAIVGYGNIGRYALDAIKAAPDMELAGVVRRSSSLGDKPAELADVPVVGSIKELTGVKVALL
CTPTRSVPEYAREILALGINTVDSYSIHGQLADLRLELDKVAKEHNAVAVISAGWDPGTDSMVRCMFE
FMAPKGITYTNFGPGMSLGHSGAVKAVKGVKNALSMIPLGTGVHRMMVYVELEPGADFAQVEKAVKT
DPYFVKDETHVIQVEDVDALIDMGNGVLMERKGVSGGTHNQLLSFSMRINNPALTAQIMVASARASVK
QKPGAYTMIQIPIIDYMYGDPDEIIRQLV (SEQ ID NO: 8)

FIG. 13

ATGGGTGAGAAGATTCGCGTGGCAATTGTTGGCTACGGCAATATCGGCCGCTACGCTTTAGATGCCAT
TAAAGCCGCCCCGGATATGGAACTGGCCGGTGTTGTGCGTCGTAGCAGCTCTTTAGGCGATAAACCGG
CAGAACTGGCCGATGTGCCGGTGGTGGGCAGCATCAAAGAGCTGACCGGTGTGAAAGTGGCTTTATTA
TGTACACCGACCCGCAGTGTGCCGGAGTATGCCCGTGAAATTCTGGCTTTAGGCATTAATACCGTGGA
TAGCTATGATATTCACGGCCAGCTGGCAGATTTACGTTTAGAACTGGATAAAGTGGCCAAGGAGCACA
ATGCAGTGGCCGTGATTAGCGCTGGTTGGGATCCGGGTACCGATAGCATGGTGCGTTGCATGTTCGAG
TTTATGGCCCCGAAAGGCATTACCTACACCAATTTCGGCCCGGGTATGTCTTTAGGTCATAGTGGTGC
CGTGAAAGCCGTGAAAGGCGTGAAGAACGCTTTAAGCATGATTATCCCGCTGGGTACCGGCGTTCACC
GCATGATGGTGTATGTGGAACTGGAACCGGGTGCCGATTTTGCCCAAGTTGAAAAAGCCGTGAAGACC
GATCCGTACTTCGTGAAGGACGAGACCCACGTGATTCAAGTTGAGGATGTGGATGCTTTAATCGATAT
GGGTAACGGCGTGCTGATGGAACGTAAAGGCGTGAGCGGCGGCACCCATAACCAGCTGCTGAGCTTTA
GCATGCGCATCAACAACCCCGCTCTGACCGCCCAGATTATGGTGGCCAGTGCCCGTGCCAGCGTGAAA
CAGAAACCGGGTGCCTACACCATGATCCAGATCCCGATCATTGACTATATGTATGGCGATCCGGATGA
AATCATCCGCCAACTGGTTTAA (SEQ ID: 13)

FIG. 14

MGEKIRVAIVGYGNIGRYALDAIKAAPDMELAGVVRRSSSLGDKPAELADVPVVGSIKELTGVKVALL
CTPTRSVPEYAREILALGINTVDSYDIHGQLADLRLELDKVAKEHNAVAVISAGWDPGTDSMVRCMFE
FMAPKGITYTNFGPGMSLCHSGAVKAVKGVKNALSMLIPLGTGVHRMMVYVELEPGADPAQVEKAVKT
DPYFVKDETHVIQVEDVDALIDMGNGVLMERKGVSGGTHNQLLSFSMRINNPALTAQIMVASARASVK
QKPGAYTMIQIPIIDYMYGDPDEIIRQLV
(SEQ ID: 14)

FIG. 15

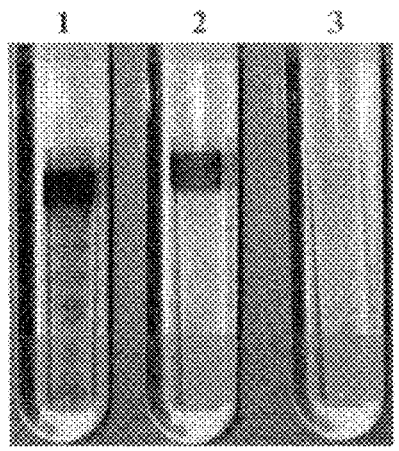

FIG. 16

D-TYPE AMINO ACID DEHYDROGENASE

TECHNICAL FIELD

There is disclosed a technique relating to a D-type amino acid dehydrogenase.

BACKGROUND ART

Proteins, which are one important component in the body, are mainly composed of 20 types of α-amino acids. Since 19 types among these have asymmetric carbon except for glycine, there are two optical isomers, D-type amino acid and L-type amino acid. Although it is known that most of the amino acids that form proteins are L-type amino acids, according to recent developments in analytical techniques, it has been clearly found that D-type amino acids are present in a trace amount in cells of higher organisms such as mammals including humans, aquatic animals, plants, and the like.

D-Type amino acids have broad industrial use as a raw material for the production of pharmaceuticals such as ovulation-inducing agents, anticoagulants, and analgesics, and also as an intermediate of industrial products such as insecticides, antibiotics, and cosmetics. Therefore, there is a need for an efficient method for producing D-type amino acid.

SUMMARY OF INVENTION

Technical Problem

An object is to provide a technique for efficient production of D-type amino acid.

Solution to Problem

In order to achieve this object, as a result of repeated intensive studies, there is provided the invention represented below.

Aspect 1.
An enzyme having the following characteristics (a) and (b):
(a) the enzyme has an activity of reversible dehydrogenation of D-amino acids;
(b) the enzyme is a hexamer of polypeptides having an amino acid sequence having 80% or greater identity to the amino acid sequence of SEQ ID NO: 2.

Aspect 2.
The enzyme according to Aspect 1, further having an activity of synthesizing D-aspartic acid from 2-oxobutanedioic acid.

Aspect 3.
The enzyme according to Aspects 1 or 2, which further has the following characteristic (c):
(c) the enzyme is capable of utilizing both NADH and NADPH as coenzymes.

Aspect 4.
The enzyme according to any one of Aspects 1 to 3, which further has the following characteristic (d):
(d) the enzyme has a $K_m$ value of 30 mM or less for $NAD^+$ in a case where meso-diaminopimelic acid is used as a substrate, and $NAD^+$ is used as a coenzyme.

Aspect 5.
The enzyme according to any one of Aspects 1 to 4, which further has the following characteristic (e):

(e): the enzyme has an optimum pH for activity of 10.5 in a case where meso-diaminopimelic acid is used as a substrate.

Aspect 6.
The enzyme according to Aspect 1, which further has the following characteristic (f):
(f): the enzyme has an optimum temperature for activity of 55° C. in a case where meso-diaminopimelic acid is used as a substrate.

Aspect 7.
The enzyme according to Aspects 1 or 2, wherein in the amino acid sequence having 80% or more identity to the amino acid sequence of SEQ ID NO: 2, the enzyme has one or more amino acid substitutions selected from the group consisting of Asp94Ser, Met154Leu, Val158Gly, Thr173Ile, Arg183Met, and His229Asn.

Aspect 8.
Polynucleotide encoding the enzyme described in any one of Aspects 1 to 7.

Aspect 9.
A vector including the polynucleotide described in Aspect 8.

Aspect 10.
A transformant containing the vector described in Aspect 9.

Aspect 11.
A method for producing the enzyme described in any one of Aspects 1 to 7 including culturing the transformant described in Aspect 10.

Aspect 12.
A method for producing D-amino acid including allowing the enzyme described in any one of Aspects 1 to 7 to act on 2-oxo acid.

Advantageous Effects of Invention

It is possible to efficiently synthesize D-type amino acid and/or 2-oxo acid.

BRIEF DESCRIPTION OF THE DRAWINGS

FIG. 1 illustrates the base sequence of DNA encoding a D-type amino acid dehydrogenase derived from *T. lipolytica*. Underlines are restriction enzyme recognition sites for cloning, and bolds are stop codons.

FIG. 2 illustrates the amino acid sequence of a D-type amino acid dehydrogenase derived from *T. lipolytica*.

FIG. 3 illustrates a result of SDS-PAGE of a crude enzyme solution, a heat-treated enzyme solution, and active fractions obtained after various chromatographies and a molecular weight marker. Lane 1 indicates the result of the molecular weight marker, Lane 2 indicates the crude enzyme solution, Lane 3 indicates the crude enzyme solution after heat treatment, Lane 4 indicates the active fraction after $Ni^+$-Chelating Sepharose™ Fast Flow chromatography, and Lane 5 indicates the active fraction after Superdex 200 gel filtration chromatography.

FIG. 4 illustrates the results of protein staining and activity-staining of a purified enzyme. Lane 1 indicates the result of the protein staining, lane 2 indicates the result of the activity-staining with $NAD^+$ for coenzyme, and lane 3 indicates the result of the activity-staining with $NADP^+$.

FIG. 11. illustrates the alignment between the amino acid sequence of D-type amino acid dehydrogenase derived from *T. lipolytica* and the amino acid sequences of other four meso-diaminopimelic acid dehydrogenases. The above other four types of meso-diaminopimelic acid dehydrogenases are those derived from *Bacillus sphaericus* (SEQ ID NO: 3), *Corynebacterium glutamicum* (SEQ ID NO: 4); *Symbiobacterium thermophilum* (SEQ ID NO: 5), and *Ureibacillus thermosphaericus* (SEQ ID NO: 6).

FIG. 12 illustrates the base sequence of DNA encoding an amino acid sequence in which six amino acid residues of D-type amino acid dehydrogenase derived from *T. lipolytica* are substituted. The squares are mutation introduction sites and the bolds are stop codons.

FIG. 13 illustrates an amino acid sequence in which six amino acid residues of D-type amino acid dehydrogenase derived from *T. lipolytica* are substituted. Squares are the mutation introduced sites.

FIG. 14 illustrates the base sequence of DNA encoding an amino acid sequence in which five amino acid residues of D-type amino acid dehydrogenase derived from *T. lipolytica* are substituted. The squares are mutation introduction sites and the bolds are stop codons.

FIG. 15 illustrates an amino acid sequence in which five amino acid residues of D-type amino acid dehydrogenase derived from *T. lipolytica* are substituted. Squares are the mutation introduced sites.

FIG. 16 illustrates the results of protein staining and activity-staining of a purified D-type amino acid dehydrogenase. Lane 1 indicates the result of the protein staining, lane 2 indicates the result of the activity-staining with D-alanine for a substrate, and lane 3 indicates the result of the activity-staining with L-alanine for a substrate.

DESCRIPTION OF EMBODIMENTS

Figure 5:
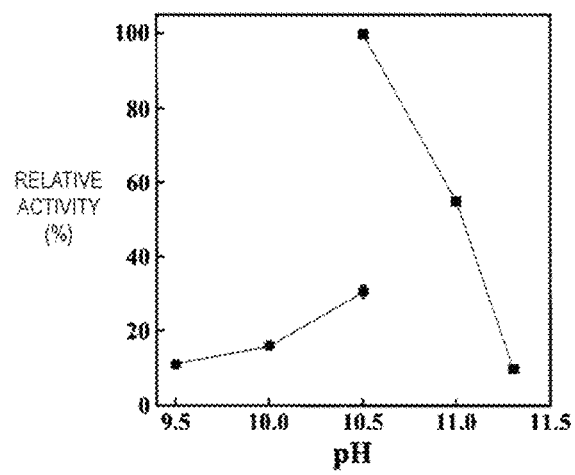
FIG. 5 illustrates a result of measurement of pH dependence of the enzyme in a deamination reaction of meso-diaminopimelic acid. Specific activity in a glycine buffer solution (pH 10.5) was calculated as 100% to calculate a relative activity at each pH. A horizontal axis indicates pH for measurement (pH) and a vertical axis indicates relative activity (%). ● represents a glycine buffer solution, and ■ represents a carbonate buffer solution, respectively.

An enzyme preferably has an activity of reversibly dehydrogenating D-type amino acid. Note that the D-type amino acid herein is also referred to as "D-amino acid" or "D amino acid". A D-type amino acid is an optical isomer of an amino acid having asymmetric carbon. The D-type amino acid herein also includes meso type amino acid (such as, meso-diaminopimelic acid) having a structure of both L and D in a molecule. In one embodiment, the D-type amino acid is not a meso-type (substantially free of L-type).

Reversible dehydrogenation of the D-type amino acid means that both a reaction of converting the D-type amino acid into corresponding oxo acid and a reaction of converting the oxo acid to corresponding D-type amino acid are catalyzed. The reaction is represented by the following formula:

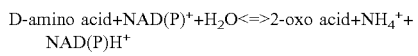

D-amino acid+NAD(P)⁺+H₂O<=>2-oxo acid+NH₄⁺+ NAD(P)H⁺

For example, in a case where the D-type amino acid is meso-diaminopimelic acid, the reaction of converting meso-diaminopimelic acid to L-2-amino-6-oxopimelic acid and the reaction of converting L-2-amino-6-oxopimelic acid to meso-diaminopimelic acid are catalyzed. Such an enzyme can also be referred to as "meso-diaminopimelic acid dehydrogenase". In one embodiment, the enzyme preferably has at least an activity of catalyzing the conversion of the oxo acid to the D-type amino acid. That is, in one embodiment, the enzyme is not necessary to have the activity of converting the D-type amino acid to the oxo acid.

The enzyme preferably has the amino acid sequence of SEQ ID NO: 2 or an amino acid sequence having identity of 60% or greater, 65% or greater, 70% or greater, 75% or greater, 80% or greater, 85% or greater, 90%, 91% or greater, 92% or greater, 93% or greater, 94% or greater, 95% or greater, 96% or greater, 97% or greater, 98% or greater, and 99% or greater with the amino acid sequence of SEQ ID NO: 2. SEQ ID NO: 2 is the amino acid sequence of D-type amino acid dehydrogenase derived from *Thermosyntropha lipolytica*.

The identity of amino acid can be calculated using analytical tools (for example, software such as FASTA, BLAST, PSI-BLAST, and SSEARCH) that are commercially available or available through the Internet. For example, the value of amino acid sequence identity (%) can be calculated by performing the search in which blastp is used for the program in Advanced BLAST 2.1, the Extract value is set to 10, all the Filters are turned off, BLOSUM62 is used for the Matrix, Gap existencecost, Per residuegapcost, and Lambdaratio are set to 11, 1, 0.85, respectively (default value), and other various parameters are set to default values.

The enzyme preferably has one or more amino acid residues selected from the group consisting of the 5th to 17th, 19th, 23rd, 27th to 35th, 37th, 49th, 51st, 54th, 56th, 58th, 63rd, 64th, 67th to 69th, 72nd, 74th, 83rd, 89th to 94th, 96th, 99th, 106th, 107th, 109th, 110th, 114th, 116th to 126th, 129th, 130th, 132nd, 138th, 145th, 146th, 148th, 149th, 151st to 153rd, 155th to 157th, 159th, 161st, 163rd, 165th to 171st, 173rd to 175th, 181st, 183rd, 186th, 187th, 190th, 192nd to 194th, 197th to 200th, 202nd, 204th, 206th, 208th, 209th, 212nd, 213rd, 215th, 218th, 226th, 227th, 229th, 230th, 233rd, 236th, 237th, 239th, 240th, 244th, 245th, 247th, 249th, 251st to 256th, 258th to 261st, 264th, 265th, 268th to 270th, 272nd, 274th, 276th, 277th, 279th to 283rd, 292nd, 299th, and 301st positions in the amino acid sequence of SEQ ID NO: 2. Here, the "1 or more amino acid residues" is, for example, preferably 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 105 or more, 110 or more 115 or more, 120 or more, 125 or more, 130 or more, 135 or more, 140 or more, 145 or more, or 150.

In one embodiment, the enzyme preferably has one or more amino acid residues selected from the group consisting of 6th, 10th to 14th, 16th, 17th, 27th to 29th, 31st, 37th, 51st, 54th, 68th, 69th, 89th, 91st, 94th, 96th, 110th, 120th, 122nd to 126th, 129th, 132nd, 146th, 149th, 151st, 153rd, 155th to 157th, 159th, 161st, 163rd, 165th, 166th, 169th, 173rd, 175th, 181st, 183rd, 187th, 193rd, 194th, 199th, 204th, 206th, 215th, 229th, 230th, 237th, 255th, 256th, 259th, 265th, 268th, 269th, 276th, 279th, and 291st positions in the amino acid sequence of SEQ ID NO: 2. Here, the "one or more amino acid residues" may be 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, 60 or more, or 63 amino acid residues. In one embodiment, it is preferable to have more amino acid residues other than the specific amino acid residues above.

In one preferable embodiment, the enzyme preferably further has one or more amino acid residues selected from the group consisting of the 5th, 7th, 9th, 15th, 23rd, 30th, 34th, 63rd, 67th, 72nd, 74th, 83rd, 90th, 92nd, 93rd, 99th, 106th, 107th, 117th to 119th, 130th, 138th, 145th, 148th, 152nd, 160th, 161st, 163rd, 167th, 170th, 174th, 186th, 190th, 198th, 202nd, 208th, 212th, 218th, 227th, 233rd, 239th, 244th, 245th, 249th, 251st, 253rd, 254th, 258th, 260th, 264th, 270th, 272nd, 280th to 283rd, and 301st positions in the amino acid sequence of SEQ ID NO: 2. Here, the "one or more amino acid residues" may be 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, or 58 amino acid residues. In one embodiment, it is preferable to have more amino acid residues other than the specific amino acid residues above.

In one more preferred embodiment, the enzyme preferably further has one or more amino acid residues selected from the group consisting of the 8th, 19th, 32nd, 33rd, 49th, 56th, 58th, 64th, 19th, 114th, 116th, 121st, 168th, 171st, 192nd, 197th, 200th, 209th, 213rd, 218th, 226th, 236th, 240th, 247th, 252nd, 261st, 274th, 277th, 292nd, and 299th positions in the amino acid sequence of SEQ ID NO: 2. Here, "one or more amino acid residues" may be 1 or more, 2 or more, 3 or more, 4 or more, 5 or more, 6 or more, 7 or more, 8 or more, 9 or more, 10 or more, 15 or more, 20 or more, 25 or more, or 29 amino acid residues.

In one embodiment, the enzyme may have one or more substitutions of the amino acid residues in Table 1 below in the amino acid sequence of SEQ ID NO: 2. Herein, "one or more" may be 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, or 85.

TABLE 1

| Position | Substituted amino acid residue |
| --- | --- |
| 5 | L |
| 7 | I |
| 8 | G |

TABLE 1-continued

| Position | Substituted amino acid residue |
| --- | --- |
| 9 | V |
| 15 | L |
| 19 | V |
| 23 | V |
| 30 | D |
| 32 | V |
| 33 | A |
| 34 | I |
| 35 | F |
| 49 | T, V |
| 56 | D |
| 58 | S |
| 63 | I |
| 64 | Q, D |
| 67 | I |
| 72 | S |
| 74 | T |
| 83 | F |
| 90 | I |
| 92 | T |
| 93 | F |
| 99 | I |
| 106 | V, M |
| 107 | N |
| 109 | A |
| 114 | G |
| 116 | A |
| 116 | A |
| 117 | S |
| 118 | L, I |
| 119 | V |
| 121 | T, V |
| 130 | I, L |
| 138 | V |
| 145 | H |
| 148 | W |
| 152 | L, V |
| 160 | L, I |
| 161 | R |
| 163 | I |
| 167 | Q, R |
| 168 | K, D |
| 170 | V |
| 171 | Q |
| 174 | L |
| 186 | W, F |
| 190 | D |
| 192 | A |
| 197 | L, R, E |
| 198 | I |
| 200 | Q, N, R, H |
| 202 | I |
| 208 | Y |
| 209 | F |
| 212 | Y |
| 213 | V |
| 218 | I |
| 218 | I |
| 226 | G |
| 227 | V |
| 233 | V |
| 236 | T, S |
| 239 | T |
| 240 | D |
| 244 | K |
| 245 | H |
| 247 | V, F, I |
| 249 | Y |
| 251 | L |
| 253 | L |
| 254 | D, E |
| 258 | F |
| 260 | S |
| 261 | S |
| 264 | I |
| 270 | A |
| 272 | R |

TABLE 1-continued

| Position | Substituted amino acid residue |
|---|---|
| 274 | Q |
| 277 | A |
| 280 | V |
| 281 | L, F |
| 282 | E, D |
| 283 | V |
| 292 | S, N |
| 299 | E, R, K |
| 301 | L |

In Table 1, "position" means the position of the amino acid residue in SEQ ID NO: 2. The "substituted amino acid residue" means a type of amino acid residue that can substitute for an amino acid residue at a specific position of SEQ ID NO: 2. In Table 1, the amino acid residue types are listed in alphabetical letters.

In one embodiment, the substitutions of the amino acid residues are preferably conservative amino acid substitutions. The "conservative amino acid substitution" means substitution of a certain amino acid residue with an amino acid residue having a side chain with similar property. The amino acid residues are classified into several families depending on the side chains thereof, namely, a basic side chain (such as lysine, arginine, and histidine), an acidic side chain (such as aspartic acid and glutamic acid), an uncharged polar side chain (such as glycine, asparagine, glutamine, serine, threonine, tyrosine, and cysteine), a non-polar side chain (such as alanine, valine, leucine, isoleucine, proline, phenylalanine, methionine, and tryptophan), a (3-branched side chain (such as threonine, valine, and isoleucine), and an aromatic side chain (such as tyrosine, phenylalanine, tryptophan, and histidine). Thus, substitution between amino acid residues within the same family is preferable.

In one embodiment, in the enzyme, one or more amino acid residues selected from the group consisting of Asp94, Met154, Val158, Thr173, Arg183, and His229 in the amino acid sequence of SEQ ID NO: 2 or an amino acid sequence having 80% or more identity thereto are preferably substituted with other amino acid residues. In one embodiment, the enzyme preferably has a substitution of one or more amino acid residues selected from the group consisting of Asp94Ser, Met154Leu, Val158Gly, Thr173Ile, Arg183Met, and His229Asn in the amino acid sequence of SEQ ID NO: 2 or an amino acid sequence having 80% or more identity thereto. Here, "Met154Leu" means that the 154th methionine residue is substituted with a leucine residue. The same applies to the other substitutions. Also, "one or more" may preferably be 2 or more, 3 or more, 4 or more, 5 or more, or 6. Thr173Ile, Arg183Met, and/or His229Asn substitutions makes it possible to produce the corresponding oxo acids and D-amino acids using a wider variety of D-amino acids and 2-oxo acids as substrates. Further, the substitution of Asp94Ser, Met154Leu and/or Val158Gly allows further increase in the catalytic efficiency.

For example, in the amino acid sequence of SEQ ID NO: 2 or an amino acid sequence having 80% or greater identity thereto, due to substitutions of Met154Leu, Val158Gly, Thr173Ile, Arg183Met, and His229Asn, the enzyme has higher activity to catalyze the following reaction using NADPH as a coenzyme compared to before mutation: a reaction of converting 2-oxo-4-methylpentanoic acid to D-leucine acid, a reaction of converting 2-oxo-3-methylpentanoic acid to D-isoleucine, a reaction of converting 2-oxo-4-(methylthio)butanoic acid to D-methionine, a reaction of converting 2-oxo-3-phenylpropanoic acid to D-phenylalanine, and a reaction of converting 2-oxooctanoic acid to D-2-aminooctanoic acid. Therefore, in the amino acid sequence of SEQ ID NO: 2 or an amino acid sequence having 80% or greater identity thereto, enzymes having substitutions of Met154Leu, Val158Gly, Thr173Ile, Arg183Met, and His229Asn are suitable for the production of D-leucine, D-isoleucine, D-methionine, D-phenylalanine, and D-2-aminooctanoic acid.

On the other hand, in the amino acid sequence of SEQ ID NO: 2 or an amino acid sequence having 80% or greater identity thereto, enzymes not having a substitution of Met154Leu, Val158Gly, Thr173Ile, Arg183Met, and His229Asn has a relatively high activity that catalyzes the following reaction: a reaction of converting 2-oxopropanoic acid to D-alanine, a reaction of converting 2-oxo-3-methylbutanoic acid to D-valine, a reaction of converting 2-oxobutanedioic acid to D-aspartic acid, a reaction of converting 2-oxoglutaric acid to D-glutamic acid, and a reaction of converting 2-oxobutanoic acid to D-2-aminobutyric acid. Therefore, the above-described enzyme having no specific mutation (substitution) is suitable for producing D-alanine, D-valine, D-aspartic acid, D-glutamic acid, and D-2-aminobutyric acid.

In one embodiment, the enzyme preferably has one or more amino acid residues selected from the group consisting of Asp94, Asp124, Met154, Gly155, Thr173, Arg183, and His229 in the amino acid sequence of SEQ ID NO: 2. Also, "one or more" may preferably be 2 or more, 3 or more, 4 or more, 5 or more, 6 or more, or 7. It is considered that existence (maintenance) of the one or more amino acid residues suitably satisfies the characteristics of $k_{cat}(min^{-1})$ and the like described below.

The enzyme is preferably a hexamer. The fact that the enzyme is hexamer means a state where six polypeptides (monomers) form one integrated structure when the enzyme is active (in an active state). The hexamer may be either a homohexamer or a heterohexamer, and is preferably a homohexamer.

In one embodiment, the enzyme preferably has the activity of producing D-aspartic acid from 2-oxobutanedioic acid. Such an enzyme may or may not have the above-described mutations of Asp94Ser, Met154Leu, Val158Gly, Thr173Ile, Arg183Met, and His229Asn in the amino acid sequence of SEQ ID NO: 2 or an amino acid sequence having 80% or greater identity thereto. In one embodiment, it is preferable that the enzyme does not have the mutations, from the viewpoint of producing more efficiently D-aspartic acid.

In one embodiment, the enzyme preferably has the activity of producing D-glutamic acid from 2-oxoglutaric acid. Such an enzyme preferably does not have the above-described mutations of Asp94Ser, Met154Leu, Val158Gly, Thr173Ile, Arg183Met, and His229Asn in the amino acid sequence of SEQ ID NO: 2 or an amino acid sequence having 80% or greater identity thereto.

It is preferable that the enzyme is capable of utilizing both NADH and NADPH as coenzymes for catalyzing a reversible dehydrogenation reaction of the D-type amino acid. The NADH is generally less expensive than the NADPH. Thus, the availability of NADH as a coenzyme is meaningful for reducing costs of manufacturing for example D-type amino acid using an enzyme.

The enzyme preferably has a $k_{cat}$ ($min^{-1}$) of $1.0 \times 10^3$ or greater when the meso-diaminopimelic acid is used as a substrate. The $k_{cat}$ ($min^{-1}$) is preferably $2.0 \times 10^3$ or greater, $3.0 \times 10^3$ or greater, $4.0 \times 10^3$ or greater, or $4.4 \times 10^3$ or greater. $k_{cat}$ is a parameter of amounts of substrates that can be catalyzed per unit time.

The enzyme preferably has a $K_m$ value of 6.0 mM or less or 5.7 mM or less when meso-diaminopimelic acid is used as a substrate. The $K_m$ value is a parameter indicating the affinity between the enzyme and the substrate. The lower the value, the higher the affinity, and the desired reaction can be efficiently performed with a small amount of enzyme.

The enzyme preferably has a $K_m$ value of 30 mM or less, 20 mM or less, or 15 mM or less for $NAD^+$ in a case where meso-diaminopimelic acid is used as a substrate and $NAD^+$ is used as a coenzyme. With such $K_m$ values, the amount of $NAD^+$ required to produce the D-amino acid or oxo acid using the enzyme can be reduced.

The enzyme preferably has a $K_m$ value of 20 mM or less, 10 mM or less, or 1 mM or less in a case where meso-diaminopymelic acid is used as a substrate and $NADP^+$ is used as a coenzyme. With such $K_m$ values, the amount of $NADP^+$ required to produce the D-amino acid or oxo acid using the enzyme can be reduced.

The enzyme preferably has an optimum pH for activity of 10.5 in a case of using meso-diaminopimelic acid as a substrate. As illustrated in FIG. 5, the optimum pH for activity of 10.5 means that the enzymatic activity is higher when the pH is 10.5 than when the pH is from 9.5 to 10.0 and the pH is from 11.0 to 11.5.

Figure 6:
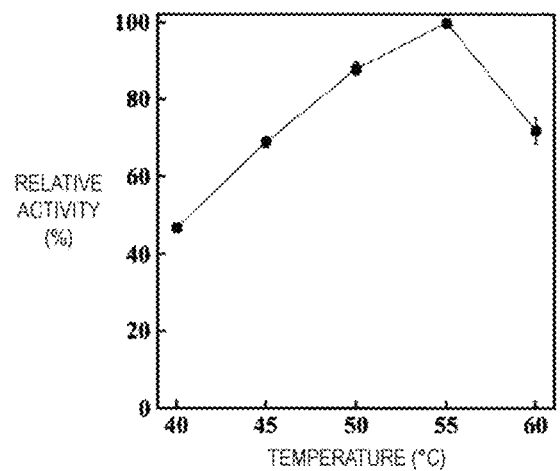
FIG. 6 illustrates a result of measurement of temperature dependence of the enzyme in the deamination reaction of meso-diaminopimelic acid. A horizontal axis indicates temperature for measurement (° C.) and a vertical axis indicates relative activity (%).

The enzyme preferably has an optimum temperature for activity of 55° C. in a case where meso-diaminopimelic acid is used as a substrate. As illustrated in FIG. 6, the optimum temperature for activity of 55° C. means that the enzymatic activity is higher at 55° C. compared to the enzymatic activity at 40° C. to 50° C. and at 60° C.

The enzyme preferably has a molecular weight of about 36 kDa as determined by SDS-PAGE of the polypeptide moiety (monomer). The "about 36 kDa" means that a range in which a person skilled in the art normally determines that there is a band at a position of 36 kDa when the molecular weight is measured by SDS-PAGE is included. The "polypeptide moiety" means polypeptide that is substantially unbound to a sugar chain.

The enzyme preferably has excellent thermal stability. For example, the enzyme preferably has activity of 95% or greater after being retained at 65° C. for 30 minutes as compared with the activity after being retained at 50° C. for 30 minutes (meso-diaminopimelic acid is used as a substrate).

The enzyme preferably has excellent pH stability. For example, the enzyme preferably has a residual activity of 90% or greater after being retained in a buffer solution at pH 5.5 to 9.5 for 30 minutes as compared with the residual activity after being retained in a buffer solution at pH 9.0 for 30 minutes.

The source of the enzyme is not particularly limited. For example, the enzyme is preferably derived from a microorganism belonging to the genus *Thermosyntropha* (for example, *Thermosyntropha lipolytica*).

The enzyme may be in a crystalline state. The enzyme in the crystalline state can be obtained, for example, according to the examples described below. The enzyme in the crystalline state is useful for purification in high purity, and stable storage and immobilization with high density and strong protease resistance.

The enzyme described above can be obtained by any method. For example, the enzyme can be obtained by utilizing a gene encoding a protein having an amino acid sequence represented in SEQ ID NO: 2 as it is (or with mutation to amino acid residues) to transform a host cell, and harvesting the protein having the above activity from the culture. In addition, the enzyme can also be obtained by chemically synthesizing polypeptide that forms the enzyme.

A structure of the polynucleotide encoding the enzyme described above is not particularly limited. For example, the polynucleotide preferably has a base sequence having identity of 60% or greater, 65% or greater, 70% or greater, 75% or greater, 80% or greater, 85% or greater, 90% or greater, 91% or greater, 92% or greater, 93% or greater, 94% or greater, 95% or greater, 96% or greater, 97% or greater, 98% or greater, and 99% or greater with the base sequence of SEQ ID NO: 1.

The identity of the base sequences can be calculated using analytical tools (such as BLAST) that are commercially available or available through an electrical communication line (Internet). When using BLAST, various parameters can be calculated at initial conditions.

The polynucleotide may be any of the DNA, RNA, or DNA-RNA hybrids. The polynucleotide is preferably isolated. In a case where the polynucleotide is DNA, it may be cDNA.

Polynucleotides can be obtained by any method. For example, it can be produced and obtained using a chemical synthesis method (for example, a solid phase synthesis method using a phophoamidite method) based on the information of SEQ ID NO: 1. It can also be readily prepared by using standard genetic engineering techniques, molecular biology techniques, biochemical techniques, and the like.

The vector preferably incorporates a polynucleotide encoding the enzyme. The type of vector is not particularly limited, and can be appropriately selected according to the type of host cell. Examples thereof include a plasmid vector, a cosmidovector, a phage vector, and a viral vector (an adenoviral vector, an adeno-associated viral vector, a retroviral vector, and a herpesvirus vector).

The vector is not limited to the configuration thereof as long as the polynucleotide can be expressed in the host. The vector preferably has other base sequences necessary for the expression of the polynucleotide. Examples of other base sequences include a promoter sequence, a leader sequence, a signal sequence, an enhancer sequence, and a ribosome binding sequence.

The transformant preferably contains a polynucleotide encoding the enzyme described above. Such a transformant can be obtained by introducing a vector containing the polynucleotide described above into the host. The host cell is not particularly limited as long as the host cell is capable of expressing the polynucleotide described above to produce the enzyme. Specific examples include a prokaryotic cell such as *E. coli* and *B. subtilis*, eukaryotic cells such as yeast, mold, insect cells, and mammalian cells. Transformation of the host using the vector can be performed according to a general method (for example, a calcium chloride method, an electroporation method, a microinjection method, and a lipofection method).

The enzyme described above can be obtained by culturing the above transformants. The culture conditions can be appropriately set according to the type of host or the like. After cultivation, the enzyme can be collected from a culture solution or a strain. In a case where an organism that secretes the enzyme out of the strain is used, the enzyme can be obtained by, for example, filtering, centrifuging, or the like to remove the insoluble matter, and then the enzyme can be obtained by performing isolation and purification by suitably combining concentration with ultrafiltration membrane, salting out dialysis such as ammonium sulfate precipitation, and various chromatographies. In this way, the enzyme described above can be mass-produced at low cost.

In one embodiment, the enzyme has excellent thermal stability. Therefore, it is useful and convenient to use the enzyme for a heat treatment in the isolation and purification. The host cells and culture supernatants obtained from the culture contain various proteins derived from the host cells. However, by performing the heat treatment, contaminant proteins derived from the host cells are denatured and condensed. In contrast, the enzyme having the excellent thermal stability does not cause denaturation, and therefore, can be easily separated from contaminant proteins derived from the host by centrifugation or the like. The conditions of the heat treatment are not particularly limited, and for example, it can be treated for 10 to 30 minutes at approximately 50° C. to 65° C. By subjecting the culture solution to the heat treatment as is or in a crude extract, other proteins can be inactivated and thereby a desired enzyme can be efficiently obtained.

The D-amino acid can be synthesized by utilizing the enzyme described above. The D-amino acid synthesis can be performed, for example, by the amination of 2-oxo acid, which is a substrate. In the presence of NADPH (or NADH) and ammonia, the enzyme can be reacted with 2-oxo acid as the substrate and the D-amino acid produced in a catalytic reaction of the enzyme can be collected. The D-amino acid collection can be performed in any method (for example, using an ion-exchange resin). Similarly, the enzyme described above can be used to produce the 2-oxo acid from the D-amino acid.

D-Alanine can be obtained by an action of the enzyme described above on 2-oxopropanoic acid. In one embodiment, the production of D-alanine preferably uses an enzyme that does not have mutations of Asp94Ser, Met154Leu, Val158Gly, Thr173Ile, Arg183Met, and His229Asn in the amino acid sequence of SEQ ID NO: 2 or an amino acid sequence having 80% or greater identity thereto.

D-Valine can be obtained by an action of the enzyme described above on 2-oxo-3-methylbutanoic acid. In one embodiment, the production of D-valine preferably uses an enzyme that does not have substitutions of Asp94Ser, Met154Leu, Val158Gly, Thr173Ile, Arg183Met and His229Asn in the amino acid sequence of SEQ ID NO: 2 or an amino acid sequence having 80% or greater identity thereto.

D-Leucine can be obtained by an action of the enzyme described above on 2-oxo-4-methylpentanoic acid. In one embodiment, the production of D-leucine preferably uses an enzyme having substitutions of Met154Leu, Val158Gly, Thr173Ile, Arg183Met, Arg183Met and His229Asn in the amino acid sequence of SEQ ID NO: 2 or an amino acid sequence having 80% or more identity thereto. Here, the enzyme may or may not have the Asp94Ser substitution in the amino acid sequence of SEQ ID NO: 2 or an amino acid sequence having 80% or more identity thereto, and in one embodiment, it preferably does not have the Asp94Ser substitution.

D-Isoleucine can be obtained by an action of the enzyme described above on 2-oxo-3-methylpentanoic acid. In one embodiment, the production of D-isoleucine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto, and in one embodiment, it preferably does not have the Asp94Ser substitution.

D-Methionine can be obtained by an action of the enzyme described above on 2-oxo-4-(methylthio) butanoic acid. In one embodiment, the production of D-methionine preferably uses an enzyme having substitutions of Met154Leu, Val158Gly, Thr173Ile, Arg183Met, and His229Asn in the amino acid sequence of SEQ ID NO: 2 or an amino acid sequence having 80% or more identity thereto. Here, the enzyme may or may not have the Asp94Ser substitution in the amino acid sequence of SEQ ID NO: 2 or an amino acid sequence having 80% or greater identity thereto. In one embodiment, the enzyme preferably does not have the Asp94Ser substitution.

D-Phenylalanine can be obtained by an action of the enzyme described above on 2-oxo-3-phenylpropanoic acid. In one embodiment, the production of D-phenylalanine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto, and in one embodiment, it preferably does not have the Asp94Ser substitution.

D-Aspartic acid can be obtained by an action of the enzyme described above on 2-oxobutanedioic acid. In one embodiment, the production of D-aspartic acid preferably uses an enzyme that does not have substitutions of Met154Leu, Val158Gly, Thr173Ile, Arg183Met, and His229Asn (or additional Asp94Ser substitution) in the amino acid sequence of SEQ ID NO: 2 or an amino acid sequence having 80% or greater identity thereto.

D-Glutamic acid can be obtained by an action of the enzyme described above on 2-oxoglutaric acid. In one embodiment, the production of D-glutamic acid preferably uses an enzyme that does not have substitutions of Met154Leu, Val158Gly, Thr173Ile, Arg183Met, and His229Asn (or even the Asp94Ser substitution) in the amino acid sequence of SEQ ID NO: 2 or an amino acid sequence having 80% or greater identity thereto.

D-2-Aminobutyric acid can be obtained by an action of the enzyme described above on 2-oxobutanoic acid. In one embodiment, the production of D-2-aminobutyric acid preferably uses an enzyme that does not have the substitutions of Asp94Ser, Met154Leu, Val158Gly, Thr173Ile, Arg183Met, and His229Asn in the amino acid sequence of SEQ ID NO: 2 or an amino acid sequence having 80% or greater identity thereto.

D-2-Aminooctanoic acid can be obtained by an action of the enzyme described above on 2-oxobutanoic acid. In one embodiment, the production of D-2-aminooctanoic acid preferably uses an enzyme having a substitution of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto, and in one embodiment, it preferably does not have the Asp94Ser substitution.

D-2-Aminoheptanoic acid can be obtained by an action of the enzyme described above on 2-oxoheptanoic acid. In one embodiment, the production of D-2-aminoheptanoic acid preferably uses an enzyme having a substitution of Met154Leu, Val158Gly, Thr173Ile, Arg183Met, and His229Asn in the amino acid sequence of SEQ ID NO: 2 or an amino acid sequence having 80% or more identity thereto. Here, the enzyme may or may not have the Asp94Ser substitution in the amino acid sequence of SEQ ID NO: 2 or an amino acid sequence having 80% or greater identity thereto.

D-Norleucine can be obtained by an action of the enzyme described above on 2-oxohexanoic acid. In one embodiment, the production of D-norleucine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Norvaline can be obtained by an action of the enzyme described above on 2-oxopentanoic acid. In one embodiment, the production of D-norvaline preferably uses an enzyme having substitutions of Met154Leu, Val158Gly, Thr173Ile, Arg183Met, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Serine can be obtained by an action of the enzyme described above on 2-oxo-3-hydroxypropionic acid. In one embodiment, the production of D-serine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Threonine can be obtained by an action of the enzyme described above on 2-3-hydroxybutanoic acid. In one embodiment, the production of D-threonine preferably uses an enzyme having substitutions of Met154Leu, Val158Gly, Thr173Ile, Arg183Met, and His229Asn in the amino acid sequence of SEQ ID NO: 2 or an amino acid sequence having 80% or more identity thereto. Here, the enzyme may or may not have the Asp94Ser substitution in the amino acid sequence of SEQ ID NO: 2 or an amino acid sequence having 80% or greater identity thereto.

D-Cysteine can be obtained by an action of the enzyme described above on 2-oxo-3-sulfanylpropanoic acid. In one embodiment, the production of D-cysteine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Asparagine can be obtained by an action of the enzyme described above on 2-oxo-3-carbamoylpropanoic acid. In one embodiment, the production of D-asparagine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Glutamine can be obtained by an action of the enzyme described above on 2-oxo-4-carbamoylbutanoic acid. In one embodiment, the production of D-glutamine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Tryptophan can be obtained by an action of the enzyme described above on 2-oxo-3-(1H-indol-3-yl) propanoic acid. In one embodiment, the production of D-tryptophan preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Lysine can be obtained by an action of the enzyme described above on 2-oxo-6-amino caproic acid. In one embodiment, the production of D-lysine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Arginine can be obtained by an action of the enzyme described above on 2-oxo-5-guanidinopentanoic acid. In one embodiment, the production of D-arginine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Tyrosine can be obtained by an action of the enzyme described above on 2-oxo-3-(4-hydroxyphenyl) propanoic acid. In one embodiment, the production of D-tyrosine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

D-Histidine can be obtained by an action of the enzyme described above on 2-oxo-3-(4-imidazolyl) propionic acid. In one embodiment, the production of D-histidine preferably uses an enzyme having substitutions of Met154Leu, Val158Gly, Thr173Ile, Arg183Met, and His229Asn in the amino acid sequence of SEQ ID NO: 2 or an amino acid sequence having 80% or greater identity thereto. Here, the enzyme may or may not have the Asp94Ser substitution in the amino acid sequence of SEQ ID NO: 2 or an amino acid sequence having 80% or greater identity thereto.

EXAMPLES

Hereinafter, the present invention will be described in detail using examples and comparative examples; however, the present invention is not limited to these examples.

Example 1 Cloning of D-Type Amino Acid Dehydrogenase Gene and Production of Expression Vector The D-type amino acid dehydrogenase gene can be obtained using known gene cloning techniques. For example, a gene can be synthesized and acquired based on sequence information that can be obtained by searching a publicly known database such as GenBank.

DNA encoding a D-type amino acid dehydrogenase derived from *T. lipolytica* having the base sequence of SEQ ID NO: 1 was obtained from GENEWIZ. This was cleaved with restriction enzymes NdeI and XhoI, separated by agarose gel electrophoresis, and then extracted and purified from the gel. The DNA fragment after the restriction enzyme treatment was incorporated into the restriction enzyme sites (NdeI and XhoI of the protein expression plasmid pET-16a (available from Novagen) by a ligation reaction, and an expression vector carrying a gene for D-type amino acid dehydrogenase was constructed. The expression vector was constructed so as to incorporate a D-type amino acid dehydrogenase gene derived from *T. lipolytica* downstream of the T7 promoter and the liposome binding site, and upstream of the T7 terminator. The base sequence (SEQ ID NO: 1) of this D-type amino acid dehydrogenase gene is illustrated in FIG. 1. In addition, the amino acid sequence (SEQ ID NO: 2) encoded by the base sequence of SEQ ID NO: 1 is also illustrated in FIG. 2.

The expression vector contains a histidine-tag. Also, when inserting the D-type amino acid dehydrogenase gene into another expression vector, a C-terminal histidine-tag can be added to the D-type amino acid dehydrogenase gene except for the stop codon (TAA is used in the present example).

Example 2 Synthesis of D-Type Amino Acid Dehydrogenase

Using the expression vector obtained in Example 1 above, *E. coli* BL21 (DE3) strain was transformed. This was inoculated into an LB medium (500 mL) containing antibiotic ampicillin (final concentration of 100 mg/L) and shaken at 37° C. until approximately $A_{600}$=0.6, and then isopropyl-beta-D(−)-galactopyranoside (available from Wako Pure Chemical Industries, Ltd.) was added to be at a final concentration of 0.1 mM, and shaken for another 6 hours at 37° C.

The strains in a culture solution were collected by centrifugation and these strains were suspended using 50 mM of a phosphate buffer solution (pH 7.2) and sonicated under ice-cooling conditions. After sonication, the obtained supernatant was set as a crude enzyme solution. The crude enzyme solution was heat-treated at 50° C. for 30 minutes, and the treated enzyme solution was purified using $Ni^+$-Chelating Sepharose™ Fast Flow chromatography (available from GE Healthcare Japan) and Superdex200 gel filtration chromatography (available from GE Healthcare Japan). The protein mass of the obtained D-type amino acid dehydrogenase was measured by a Bradford method.

FIG. 3 illustrates a result of SDS-PAGE of a crude enzyme solution, a heat-treated enzyme solution, and active fractions obtained after various chromatographies and a molecular weight marker. From Lane 5 in FIG. 1, a single band of protein was confirmed at a position of 36 kDa, and a good purification result was obtained.

Example 3 Confirmation of Coenzyme Dependence of D-Type Amino Acid Dehydrogenase The coenzyme dependence was evaluated for the D-type amino acid dehydrogenase obtained in Example 2 above. The coenzyme dependence of the enzyme was evaluated by an activity-staining method due to an enzymatic catalytic reaction.

More specifically, an appropriate amount of enzyme solution was subjected to disc gel electrophoresis. The gel after electrophoresis was immersed in a reaction solution containing 200 mM phosphate buffer solution (pH 8.0), 10 mM meso-diaminopimelic acid (pH8.0), 0.1 mM 2-(4-iodophenyl)-3-(4-nitrophenyl)-5-phenyl-2H-tetrazolium chloride (INT) (available from Dojindo Molecular Technologies, Inc.), 0.04 mM 1-methoxy-5-methylphenazinium methylsulfate (PMS) (available from Dojindo Molecular Technologies, Inc.), and 1.25 mM coenzymes, and incubated at 50° C. for 30 minutes. The 2-(4-iodophenyl)-3-(4-nitrophenyl)-5-phenyl-2H-tetrazolium chloride in the reaction solution is reduced to form a water-soluble formazan. A reaction formula is indicated below. In the following reaction formula, the D-type amino acid dehydrogenase is referred to as "meso-DAPDH".

[Chemical Formula 1]

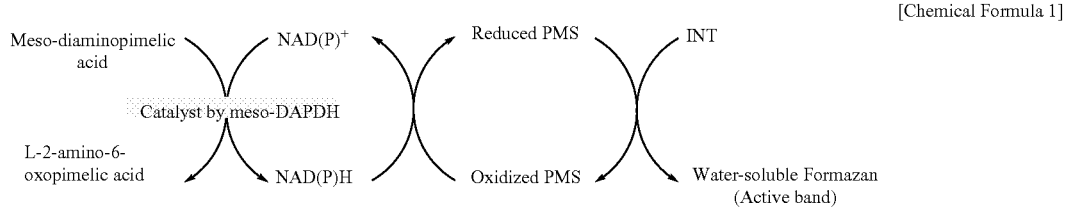

FIG. 4 illustrates the results of protein staining and activity-staining of a purified enzyme. A single band due to the enzyme was confirmed from each lane in FIG. 4. It was also confirmed from lanes 2 and 3 that the enzyme utilized both $NAD^+$ and $NADP^+$ coenzymes.

Example 4 Confirmation of Optimum pH in Catalytic Reaction of D-Type Amino Acid Dehydrogenase The optimum pH was evaluated for the D-type amino acid dehydrogenase obtained in Example 2. The activity of the enzyme was measured by determining an increase in absorbance at wavelength of 340 nm of NADPH produced by the enzymatic catalytic reaction.

More specifically, the reaction solution was prepared by mixing an appropriate amount of enzyme solution in 200 mM various buffer solutions containing 10 mM meso-diaminopimelic acid and 1.25 mM $NADP^+$. Next, the activity was assayed by measuring the increase in absorbance at 340 nm with changes from $NADP^+$ to NADPH in this reaction solution at a reaction temperature of 50° C.

The absorbance was measured by an ultraviolet-visible spectrophotometer UV-1800 (available from SHIMADZU).

The specific activity of the enzyme was calculated from the concentration of the enzyme used and enzyme dilution rate using the obtained absorbance change and the following equation.

$$\text{Specific activity} = \frac{\Delta A340 \cdot D}{6.22 \cdot C \cdot d} \quad \text{(Equation 1)}$$

ΔA340: Amount of absorbance change per minute at 340 nm
D: Enzyme dilution rate
6.22: Millimolar molecular absorptivity (L·mmol$^{-1}$·cm$^{-1}$) of NADPH at 340 nm
C: Protein concentration (mg/mL)
D: Optical path length (1 cm)

The measurement results are illustrated in FIG. 5. The results indicate that the optimum pH for activity in the deamination of meso-diaminopimelic acid is 10.5.

Example 5 Confirmation of Optimum Temperature in Catalytic Reaction of D-Type Amino Acid Dehydrogenase The absorbance was measured in the same manner as in Example 4 except that 1.25 mM of NADP$^+$ was added to the reaction solution heated at a predetermined temperature (50° C., 55° C., 60° C., 65° C., 70° C., 75° C., or 80° C.) and the increase in absorbance was immediately measured to determine the relative activity. The measurement results are illustrated in FIG. 6. From this result, it was confirmed that the optimum temperature for activity is about 55° C.

Example 6 Confirmation of Thermal Stability of D-Type Amino Acid Dehydrogenase The D-type amino acid dehydrogenase purified in Example 2 was heat-treated for 30 minutes under various temperature conditions (50, 55, 60, 65, or 70° C.) in 10 mM phosphate buffer solution (pH 7.2), and the residual activity after standing for 5 minutes in ice was confirmed. Enzymatic activity was assessed by the increase in absorbance at 340 nm due to the formation of NADPH when meso-diaminopimelic acid was used as a substrate by the method described in Example 4. The residual activity after treatment at other temperatures was calculated as a relative activity, with the activity at 50° C. as 100%.

Figure 7:
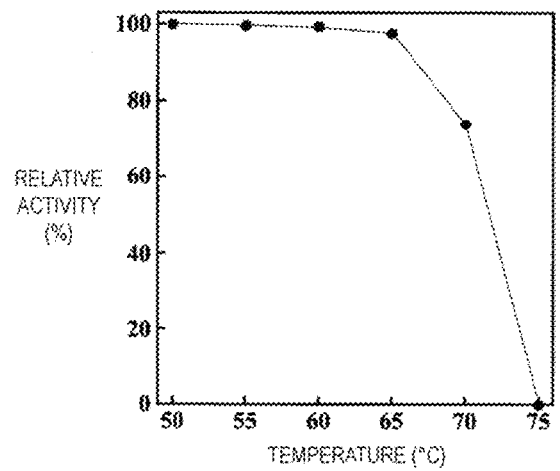
FIG. 7 illustrates a result of measurement of thermostability of the enzyme. A horizontal axis indicates a heat treatment temperature (° C.) and a vertical axis indicates relative activity (%).

The measurement results are illustrated in FIG. 7. From this result, it was confirmed that the enzyme retained a residual activity of about 74% after heat treatment at 70° C.

Example 7 Confirmation of pH Stability of D-Type Amino Acid Dehydrogenase

The D-type amino acid dehydrogenase purified in Example 2 was heat-treated at 50° C. for 30 minutes in each 100 mM buffer solution (pH 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, or 11.3), and the residual activity after standing for 5 minutes in ice was confirmed. Enzymatic activity was assessed by the increase in absorbance at 340 nm due to the formation of NADPH when meso-diaminopimelic acid was used as a substrate by the method described in Example 4. The activity in the treatment at pH 9.0 was defined as 100%, and the residual activity after the treatment at other pH was calculated as the relative activity.

Figure 8:
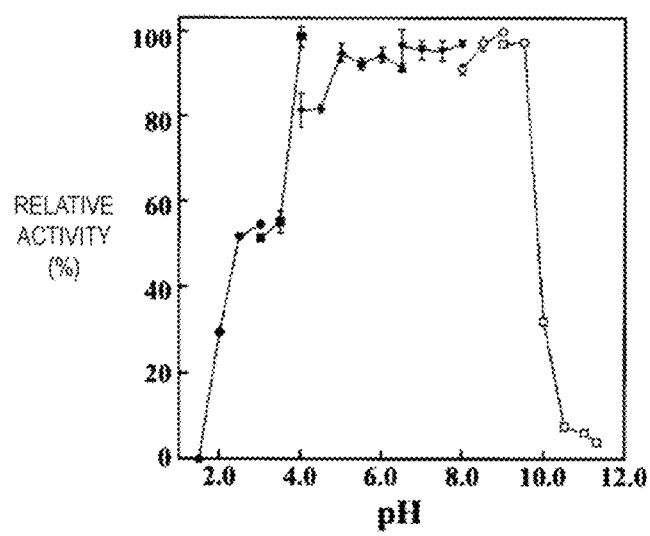
FIG. 8 illustrates a result of measurement of pH stability of the enzyme. A horizontal axis is temperature for measurement (pH) and a vertical axis is relative activity (%). ● represents phosphate buffer solution, ■ represents formate buffer solution, ♦ represents acetate buffer solution, ▲ represents citrate buffer solution, ▼ represents phosphate buffer solution, ○ represents borate buffer solution, and □ represents carbonate buffer solution.

The measurement results are illustrated in FIG. 8. As illustrated in FIG. 8, the D-type amino acid dehydrogenase retained a residual activity of about 90% or greater after treatment at pH 5.0 to 9.5.

Example 8 Kinetic Analysis of D-Type Amino Acid Dehydrogenase

For the D-type amino acid dehydrogenase obtained in Example 2, a kinetic analysis was performed by using meso-diaminopimelic acid as a substrate, and NADP$^+$ or NAD$^+$ as the coenzyme.

A turnover number ($k_{cat}$) as a reaction rate parameter, a Michaelis constant ($K_m$) value, and catalytic efficiency ($k_{cat}/K_m$) were determined with Igor Pro ver. 3.14 (available from WaveMetrics) based on Michaelis-Menten equation after the initial velocities were plotted against different substrates and coenzyme concentrations. Enzymatic activity was evaluated by the increase in the absorbance at 340 nm due to the formation of NAD(P)H in a case of using meso-diaminopimelic acid as a substrate in the method described in Example 4.

Table 2 indicates the kinetic analysis results for the purified enzyme. As indicated in Table 2, in the D-type amino acid dehydrogenase, the use of NADP$^+$ for the coenzyme rather than NAD$^+$ resulted in higher catalytic efficiencies.

TABLE 2

| Kinetic analysis | | | |
|---|---|---|---|
| Substrate Coenzyme | $k_{cat}$ (min$^{-1}$) | $K_m$ (mM) | $k_{cat}/K_m$ (min$^{-1}$·mM$^{-1}$) |
| Meso-diaminopimelic acid | 4.42 × 10$^3$ | 5.68 | 7.78 × 10$^2$ |
| NAD$^+$ | 4.65 × 10$^3$ | 14.8 | 3.13 × 10$^2$ |
| NADP$^+$ | 4.98 × 10$^3$ | 0.828 | 6.01 × 10$^3$ |

The $k_{cat}$, $K_m$, and $k_{cat}/K_m$ for meso-diaminopimelic acid were determined using NADP$^+$ as the coenzyme.

Example 9 Crystallization of D-Type Amino Acid Dehydrogenase

Figure 9:
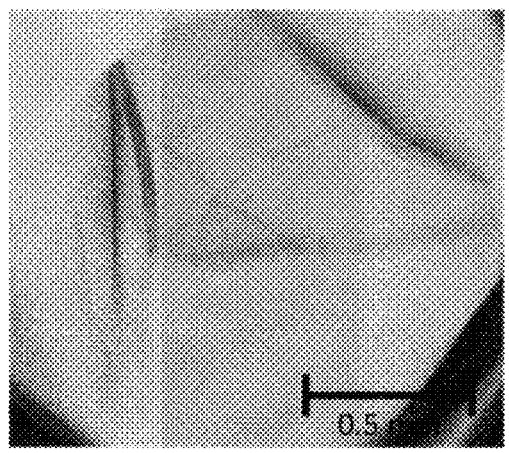
FIG. 9 illustrates the crystal of D-type amino acid dehydrogenase derived from *T. lipolytica*.

The purified D-type amino acid dehydrogenase solution (concentration 10.64 mg/mL) was mixed with the same amount (0.5 μL each) of the crystallization solution composed of 0.2 M potassium chloride and 20% w/v polyethylene glycerol 3350. On a 96 well plate (Hampton Research Co., Ltd.), 50 μL of the crystallization solution which was set as a mother liquor was left to stand at 20° C. by a vapor diffusion using a sitting drop method. Crystals precipitated after 1 day and grew to crystals of measurable size (approximately 1.5×1.0×1.0 mm) after 3 days (FIG. 9).

Example 10 Crystal Structure Analysis of D-Type Amino Acid Dehydrogenase

Since the crystal deteriorated due to X-ray damage and a resolution gradually decreased in a room temperature measurement, the crystal of the D-type amino acid dehydrogenase was measured under the low temperature condition. After the crystal was transferred to a crystallization solution containing 30% glycerol, 90K nitrogen gas was purged into the crystallized solution and rapidly cooled. X-ray diffraction data with 2.30 Å resolution was collected using an X-ray diffractometer MX300HE detector (available from Raynonix) to determine crystallographic parameters. The space group was C2 and the lattice constant was a=132.88 Å, b=100.45 Å, c=83.27 Å, α=90°, β=110.01°, and γ=90°. Assuming that the asymmetric unit contains six molecules, the solvent content of the crystals was 54.1%.

Example 11 Solid Structure Determination of D-Type Amino Acid Dehydrogenase

The X ray diffraction intensity data obtained in Example 10 was used to carry out a molecular replacement method using a program PHASER for determining the three dimensional structure of D-type amino acid dehydrogenase. The three-dimensional structural coordinates of meso-DAPDH derived from *Symbiobacterium thermophilum* were used as a search model for calculation of molecular replacement. As a result of calculation using X-ray diffraction intensity data from 50.0 Å to 2.30 Å resolution, one kind of significant solution was obtained.

As a result of refinement of the obtained structural model using a structural factor with a resolution of 30.0 Å to 2.30 Å by the method of restraint refinement in the program REFMAC5. The amino acid residues of Lys4-Val301 were assigned in both A and B molecules. Additionally, 332 water molecules were assigned by the electron density map. At the final stage of refinement, the R factor was 19.3% and the Free-R factor was 24.7%. Furthermore, the root mean square deviation from the ideal state of the bond distance and the bond angle between the atoms were 0.01 Å and 1.68 degrees, respectively.

Figure 10:
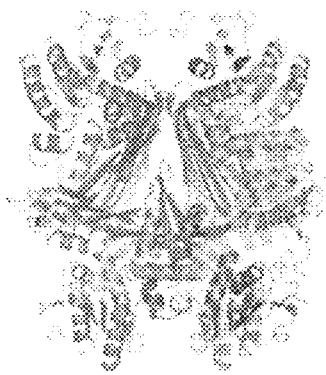
FIG. 10 illustrates the three-dimensional structure of D-type amino acid dehydrogenase derived from *T. lipolytica*.

The three-dimensional structural coordinates were obtained by the analysis above. From the obtained structural coordinates, it was confirmed that the oligomeric state of the D-type amino acid dehydrogenase was a hexamer (FIG. 10).

Example 12 Synthesis of Modified D-Type Amino Acid Dehydrogenase

DNA encoding a mutant enzyme polypeptide, into which six types of mutations (Asp94Ser, Met154Leu, Val158Gly, Thr173Ile, Arg183Met, and His229Asn) have been introduced into the amino acid sequence of D-type amino acid dehydrogenase derived from *T. lipolytica* was obtained by synthesis. Using this as a template, the gene of the enzyme was amplified by PCR using "PrimeSTAR Max DNA Polymerase" available from Takara Bio Inc. PCR was performed according to the manufacturer's instructions. The PCR reaction solution was prepared so as to contain 0.3 μM of each of the following primers and 50 ng of the above-described template DNA.

```
                                          (SEQ ID NO: 9)
5'-CACCATGGGTGAGAAGATTCGCGTGGCAAT-3'

(SEQ ID NO: 10)
5'-TTAAACCAGTTGGCGGATGATTTCATCCGG-3'
```

The reaction solution after PCR was purified by Wizard SV Gel and PCR Clean-Up System (available from Promega Corporation), and the PCR amplification product was confirmed by agarose gel electrophoresis. As a result, it was confirmed that the expected amplification product (about 0.9 kbp) was obtained.

According to the manufacturer's protocol, the purified amplification product was incorporated into a pET100 vector (I available from Invitrogen) of a plasmid for protein expression to construct a six-mutation D-type amino acid dehydrogenase/pET100. The expression vector was constructed so as to incorporate a six-mutation D-type amino acid dehydrogenase gene derived from *T. lipolytica* downstream of the T7 promoter and liposome binding site, and upstream of the T7 terminator. FIG. 12 illustrates the base sequence (SEQ ID NO: 7) of this six-mutation D-type amino acid dehydrogenase gene. In addition, the amino acid sequence (SEQ ID NO: 8) encoded by the base sequence of SEQ ID NO: 7 is also illustrated in FIG. 13.

The expression vector contains a histidine-tag. Alternatively, when inserting the mutant D-type amino acid dehydrogenase gene into another expression vector, a C-terminal histidine-tag can also be added to the D-type amino acid dehydrogenase gene except for the stop codon (TAA is used in the present example).

In order to produce a gene of a mutant enzyme in which five types of mutations were introduced into D-type amino acid dehydrogenase derived from *T. lipolytica*, the expression vector was prepared by PCR using the six-mutation D-type amino acid dehydrogenase/pET100 prepared above as a template, using "PrimeSTAR Max DNA Polymerase" available from Takara Bio Inc., PCR was performed according to the manufacturer's protocol. The PCR reaction solution was prepared so as to contain 0.3 μM of each of the following primers and 50 ng of the above-described template DNA.

```
                                         (SEQ ID NO: 11)
5'-CCGTGGATAGCTATGATATTCACGGCCAGC-3'

(SEQ ID NO: 12)
5'-GCTGGCCGTGAATATCATAGCTATCCACGG-3'
```

After PCR, 2 μL of DpnI was added to the reaction solution and treated at 37° C. for 1 hour, and *E. coli* DH5α was transformed using the solution after treatment. Transformed cells were coated on an LB agar plate containing antibiotic ampicillin (final concentration 100 mg/L) and cultured at 37° C. for 16 hours. The generated colonies were harvested and cultured in LB liquid medium containing ampicillin overnight. The strains were collected from the culture solution by centrifugation, and five-mutation D-type amino acid dehydrogenase/pET100 was collected according to the manufacturer's protocol using AccuPrep Plasmid Mini Extraction Kit (BIONEER). FIG. 14 illustrates the base sequence of the five-mutation D-type amino acid dehydrogenase gene (SEQ ID NO: 13). In addition, FIG. 15 illustrates the amino acid sequence (SEQ ID NO: 14) encoded by the base sequence of SEQ ID NO: 13.

Using the expression vector or D-type amino acid dehydrogenase/pET-16b(+) obtained above, *E. coli* BL21 (DE3) strain was transformed respectively. These were inoculated into 250 mL of Overnight Express Instant LB medium containing ampicillin (available from Merck Millipore) and cultured for 16 hours at 37° C.

The strains in a culture solution were collected by centrifugation and these strains were suspended using 50 mM of a phosphate buffer solution (pH 7.2) and sonicated under ice-cooling conditions. After sonication, the obtained supernatant was used as a crude enzyme solution. The crude enzyme solution was heat-treated at 50° C. for 30 minutes, and the treated enzyme solution was purified using Ni$^+$-Chelating Sepharose™ Fast Flow chromatography (available from GE Healthcare Japan) and Superdex200 gel filtration chromatography (available from GE Healthcare Japan). The concentration of the obtained D-type amino acid dehydrogenase was measured by a Bradford method.

Example 13 Confirmation of Activity of D-Type Amino Acid Dehydrogenase

The activity was evaluated for the D-type amino acid dehydrogenase obtained in Example 2 above. The activity of the enzyme was evaluated by an activity-staining method due to a catalytic reaction of the enzyme. More specifically, an appropriate amount of enzyme solution was subjected to disc gel electrophoresis. The gel after electrophoresis was immersed in a reaction solution containing 200 mM of phosphate buffer solution (pH 8.0), 10 mM of D-alanine or L-alanine, 0.1 mM of 2-(4-iodophenyl)-3-(4-nitrophenyl)-5-phenyl-2H-tetrazolium chloride (INT) (available from Dojindo Molecular Technologies, Inc.), 0.04 mM of 1-methoxy-5-methylphenazinium methyl sulfate (PMS) (available from Dojindo Molecular Technologies, Inc.), and 1.25 mM of NADP$^+$, and kept at 50° C. for 30 minutes. The 2-(4-iodophenyl)-3-(4-nitrophenyl)-5-phenyl-2H-tetrazolium chloride in the reaction solution is reduced to form a water-soluble formazan. A reaction formula is indicated below. In the following reaction formula, the D-type amino acid dehydrogenase is referred to as "meso-DAPDH".

[Chemical Formula 2]

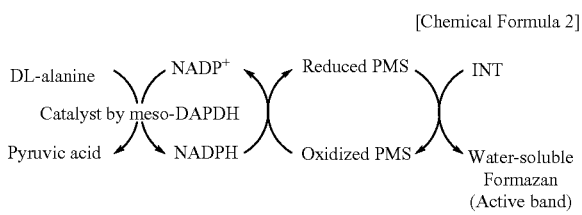

FIG. 16 illustrates the results of protein staining and activity-staining of the purified D-type amino acid dehydrogenase. From lanes 1 and 2 in FIG. 16, a single band due to the enzyme was confirmed. From lane 2, it was also confirmed that the enzyme selectively acts on the D-amino acid. Also, the D-type amino acid dehydrogenase reversibly catalyzes the deamination of the D-amino acid. Therefore, it was confirmed that the D-type amino acid dehydrogenase synthesized the D-amino acid rather than the L-amino acid by amination of 2-oxo acid.

Example 14 Confirmation of D-Amino Acid Synthesis Activity of Each Enzyme

The D-amino acid synthesis activity of the enzymes obtained in Examples 2 and 12 was measured, and the effect of mutation on D-amino acid synthesis activity was examined. The activity of the enzyme was measured by determining a decrease in absorbance at wavelength of 340 nm of NADPH or NADH produced by the catalytic reaction of the enzyme and determining the enzymatic activity by the determined decrease in absorbance as an indicator. More specifically, a reaction solution was prepared by mixing an appropriate amount of the enzyme solution in 200 mM of glycine buffer solution (pH 9.5) containing 5 mM of 2-oxoacid, 0.1 mM of NAD(P)H, and 200 mM of ammonium chloride. Next, the activity was assayed by measuring the decrease in absorbance at 340 nm with changes from NAD(P)H to NAD(P)$^+$ in this reaction solution at a reaction temperature of 50° C. The absorbance was measured by an ultraviolet-visible spectrophotometer UV-1800 (available from SHIMADZU). The enzymatic activity was assayed by measuring absorbance change and using the same equation as used in Example 4, and the specific activity of the enzyme was then calculated from the concentration of the enzyme used and the enzyme dilution rate. Table 3 illustrates the D-amino acid synthesis activity of each enzyme.

TABLE 3

| | Wild type | | Five-mutation enzyme | | Six-mutation enzyme | |
| --- | --- | --- | --- | --- | --- | --- |
| 2-Oxo acid/synthesized D-amino acid | NADPH μmol/min/mg | NADH μmol/min/mg | NADPH μmol/min/mg | NADH μmol/min/mg | NADPH μmol/min/mg | NADH μmol/min/mg |
| 2-oxopropanoic acid/ D-alanine | 5.3 ± 0.038 | 0.49 ± 0.016 | 0.071 ± 0.00074 | 0.0077 ± 0.0015 | 0.044 ± 0.0034 | 0.0053 ± 0.0036 |
| 2-oxo-3-methylbutanoic acid/D-valine | 0.33 ± 0.0094 | 0.43 ± 0.0026 | 0.11 ± 0.0034 | 0.18 ± 0.00078 | 0.058 ± 0.0027 | 0.18 ± 0.00089 |
| 2-oxo-4-methylpentanoic acid/D-leucine | 0.061 ± 0.00082 | 0.27 ± 0.0064 | 0.20 ± 0.0071 | 0.11 ± 0.0027 | 0.11 ± 0.0013 | No Activity |
| 2-oxo-3-methylbutanoic acid/D-isoleucine | 0.060 ± 0.0022 | 0.33 ± 0.0064 | 0.10 ± 0.0013 | 0.13 ± 0.0021 | 0.052 ± 0.0063 | 0.13 ± 0.00078 |
| 2-oxo-4-(methylthio) butanoic acid/D-methionine | 0.059 ± 0.0065 | 0.0033 ± 0.0016 | 0.18 ± 0.0022 | No Activity | 0.089 ± 0.0038 | No Activity |
| 2-oxo-3-phenylpropanoic acid/D-phenyl alanine | No Activity | 0.020 ± 0.0053 | 0.068 ± 0.0039 | No Activity | 0.036 ± 0.0037 | No Activity |
| 2-oxobutanedioic acid/D-aspartic acid | 5.7 ± 0.60 | 0.43 ± 0.015 | 0.60 ± 0.035 | 0.14 ± 0.014 | 0.32 ± 0.0082 | 0.12 ± 0.010 |
| 2-oxoglutaric acid/ D-glutamic acid | 0.27 ± 0.010 | No Activity | 0.039 ± 0.0073 | No Activity | 0.067 ± 0.0046 | No Activity |
| 2-oxobutanoic acid/ D-2-aminobutyric acid | 2.3 ± 0.030 | 0.13 ± 0.0041 | 0.13 ± 0.0020 | 0.044 ± 0.0049 | 0.077 ± 0.0041 | 0.032 ± 0.0023 |
| 2-oxooctanoic acid/ D-2-aminooctanoic acid | 0.101 ± 0.010 | No Activity | 0.47 ± 0.012 | 0.017 ± 0.0027 | 0.35 ± 0.0093 | 0.0098 ± 0.0047 |

From the results in Table 3, D-type amino acid dehydrogenase without mutation uses various 2-oxo acids as substrates to synthesize various D-amino acids such as branched D-amino acids, sulfur-containing D-amino acids, and acidic D-amino acids. In addition, by introducing a mutation into the D-type amino acid dehydrogenase, the NAD(P)H-dependent synthesis activity of branched D-amino acids increased about three times. Further, a new finding of NADPH-dependent aromatic D-amino acid synthesis activity, which was not detected in the enzyme before mutation introduction, was confirmed.

SEQUENCE LISTING

P18-161WO_PCT_D-type amino acid dehydrogenase_20180808_160159_6. txt

The invention claimed is:

1. An enzyme having the following characteristics (a) and (b):
   (a) the enzyme has an activity of reversible dehydrogenation of D-amino acids; and (b) the enzyme is a hexamer of polypeptides having an amino acid sequence having 80% or greater identity to the amino acid sequence of SEQ ID NO: 2: and wherein, in the amino acid sequence having 80% or greater identity to the amino acid sequence of SEQ ID NO: 2, the enzyme has one or more amino acid substitutions selected from the group consisting of Asp94Ser, Met154Leu, Val158Gly, Thr173Ile, Arg183Met, and His299Asn.

2. The enzyme according to claim 1, which has an activity of synthesizing D-aspartic acid from 2-oxobutanedioic acid.

3. The enzyme according to claim 1, which further has the following characteristic (c):
   (c) the enzyme is capable of utilizing both NADH and NADPH as coenzymes.

4. The enzyme according to claim 1, which further has the following characteristic (d):
   (d) the enzyme has a $K_m$ value of 30 mM or less for $NAD^+$ in a case where meso-diaminopimelic acid is used as a substrate, and $NAD^+$ is used as a coenzyme.

5. The enzyme according to claim 1, which further has the following characteristic (e):
   (e): an optimum pH of the enzyme is 10.5 in a case where meso-diaminopimelic acid is used as a substrate.

6. The enzyme according to claim 1, which further has the following characteristic (f):
   (f): an optimum temperature of the enzyme is 55° C. in a case where meso-diaminopimelic acid is used as a substrate.

7. The enzyme according to claim 1, wherein the amino acid sequence of the enzyme is at least 90% sequence identical to the amino acid sequence of SEQ ID NO: 2.

8. A method for producing a 2-oxo acid comprising allowing the enzyme described in claim 1 to act on a D-amino acid.

* * * * *

SEQUENCE LISTING

<160> NUMBER OF SEQ ID NOS: 14

<210> SEQ ID NO 1
<211> LENGTH: 915
<212> TYPE: DNA
<213> ORGANISM: Thermosyntropha lipolytica

<400> SEQUENCE: 1

```
catatgggcg aaaagataag agtagctatt gtgggttatg gcaatatagg aagatatgct      60
ttagatgcta taaaggcagc tcctgatatg gaattagccg gggtagttcg caggtcttca     120
tctctggggg ataagccggc agaactggct gatgtgccga tagtagggtc tattaaggaa     180
cttacagggg taaaggtagc cctttttatgt accccctaccc gttcagtacc ggagtatgcc    240
agagagattt tagctcttgg cattaatacg gttgacagtt atgatattca tggccagtta     300
gctgatttac gattggaatt agataaagtt gccaaggaac ataatgcagt agcggtgata     360
tcagccggct gggatccggg aactgattcc atggtgcgct gtatgtttga atttatggct     420
cccaaaggta taacctacac caattttggc cccggcatga gcatggggca ctcggtagcc     480
gtaaaggcgg ttaaagggt taaaaatgcc ctttctatga ctataccttt aggcaccggt      540
gtgcatcggc gcatggttta tgtggaatta gaaccgggag ctgattttgc ccaggtagaa     600
aaggcagtaa aaactgatcc ctattttgta aaagatgaaa ctcatgtcat ccaggtagaa     660
gatgttgatg ccttatcga tatgggacat ggagtattga tggaaagaaa aggagtatct     720
ggcggtaccc acaatcagtt gttaagtttt tccatgcgca taaacaatcc ggctttaact     780
gctcagataa tggtagcttc ggccagagcc agtgtaaaac agaaacctgg tgcttatact     840
atgattcaga taccgataat agactatatg tatggagatc ctgacgaaat tatccgccag     900
cttgtataac tcgag                                                      915
```

<210> SEQ ID NO 2
<211> LENGTH: 301
<212> TYPE: PRT
<213> ORGANISM: Thermosyntropha lipolytica

<400> SEQUENCE: 2

```
Met Gly Glu Lys Ile Arg Val Ala Ile Val Gly Tyr Gly Asn Ile Gly
1               5                   10                  15

Arg Tyr Ala Leu Asp Ala Ile Lys Ala Ala Pro Asp Met Glu Leu Ala
            20                  25                  30

Gly Val Val Arg Arg Ser Ser Ser Leu Gly Asp Lys Pro Ala Glu Leu
        35                  40                  45

Ala Asp Val Pro Val Val Gly Ser Ile Lys Glu Leu Thr Gly Val Lys
    50                  55                  60

Val Ala Leu Leu Cys Thr Pro Thr Arg Ser Val Pro Glu Tyr Ala Arg
65                  70                  75                  80

Glu Ile Leu Ala Leu Gly Ile Asn Thr Val Asp Ser Tyr Asp Ile His
                85                  90                  95
```

```
Gly Gln Leu Ala Asp Leu Arg Leu Glu Leu Asp Lys Val Ala Lys Glu
            100                 105                 110

His Asn Ala Val Ala Val Ile Ser Ala Gly Trp Asp Pro Gly Thr Asp
            115                 120                 125

Ser Met Val Arg Cys Met Phe Glu Phe Met Ala Pro Lys Gly Ile Thr
130                 135                 140

Tyr Thr Asn Phe Gly Pro Gly Met Ser Met Gly His Ser Val Ala Val
145                 150                 155                 160

Lys Ala Val Lys Gly Val Lys Asn Ala Leu Ser Met Thr Ile Pro Leu
                165                 170                 175

Gly Thr Gly Val His Arg Met Val Tyr Val Glu Leu Glu Pro Gly
            180                 185                 190

Ala Asp Phe Ala Gln Val Glu Lys Ala Val Lys Thr Asp Pro Tyr Phe
            195                 200                 205

Val Lys Asp Glu Thr His Val Ile Gln Val Glu Asp Val Asp Ala Leu
            210                 215                 220

Ile Asp Met Gly His Gly Val Leu Met Glu Arg Lys Gly Val Ser Gly
225                 230                 235                 240

Gly Thr His Asn Gln Leu Leu Ser Phe Ser Met Arg Ile Asn Asn Pro
                245                 250                 255

Ala Leu Thr Ala Gln Ile Met Val Ala Ser Arg Ala Ser Val Lys
            260                 265                 270

Gln Lys Pro Gly Ala Tyr Thr Met Ile Gln Ile Pro Ile Ile Asp Tyr
            275                 280                 285

Met Tyr Gly Asp Pro Asp Glu Ile Ile Arg Gln Leu Val
            290                 295                 300
```

<210> SEQ ID NO 3
<211> LENGTH: 326
<212> TYPE: PRT
<213> ORGANISM: Bacillus sphaericus

<400> SEQUENCE: 3

```
Met Ser Ala Ile Arg Val Gly Ile Val Gly Tyr Gly Asn Leu Gly Arg
1               5                   10                  15

Gly Val Glu Phe Ala Ile Ser Gln Asn Pro Asp Met Glu Leu Val Ala
            20                  25                  30

Val Phe Thr Arg Arg Asp Pro

Lys Asp Ala Val Glu Arg Val Arg Asn Gly Glu Asn Pro Glu Leu Thr
            180                 185                 190

Thr Arg Glu Lys His Ala Arg Glu Cys Trp Val Val Leu Glu Glu Gly
        195                 200                 205

Ala Asp Ala Pro Lys Val Glu Gln Glu Ile Val Thr Met Pro Asn Tyr
    210                 215                 220

Phe Asp Glu Tyr Asn Thr Thr Val Asn Phe Ile Ser Glu Asp Glu Phe
225                 230                 235                 240

Asn Ala Asn His Thr Gly Met Pro His Gly Gly Phe Val Ile Arg Ser
                245                 250                 255

Gly Glu Ser Gly Ala Asn Asp Lys Gln Ile Leu Glu Phe Ser Leu Lys
            260                 265                 270

Leu Glu Ser Asn Pro Asn Phe Thr Ser Ser Val Leu Val Ala Tyr Ala
        275                 280                 285

Arg Ala Ala His Arg Leu Ser Gln Ala Gly Glu Lys Gly Ala Lys Thr
    290                 295                 300

Val Phe Asp Ile Pro Phe Gly Leu Leu Ser Pro Lys Ser Ala Ala Gln
305                 310                 315                 320

Leu Arg Lys Glu Leu Leu
                325

<210> SEQ ID NO 4
<211> LENGTH: 320
<212> TYPE: PRT
<213> ORGANISM: Corynebacterium glutamicum

<400> SEQUENCE: 4

Met Thr Asn Ile Arg Val Ala Ile Val Gly Tyr Gly Asn Leu Gly Arg
1               5                   10                  15

Ser Val Glu Lys Leu Ile Ala Lys Gln Pro Asp Met Asp Leu Val Gly
            20                  25                  30

Ile Phe Ser Arg Arg Ala Thr Leu Asp Thr Lys Thr Pro Val Phe Asp
        35                  40                  45

Val Ala Asp Val Asp Lys His Ala Asp Val Asp Val Leu Phe Leu
    50                  55                  60

Cys Met Gly Ser Ala Thr Asp Ile Pro Glu Gln Ala Pro Lys Phe Ala
65                  70                  75                  80

Gln Phe Ala Cys Thr Val Asp Thr Tyr Asp Asn His Arg Asp Ile Pro
                85                  90                  95

Arg His Arg Gln Val Met Asn Glu Ala Ala Thr Ala Ala Gly Asn Val
            100                 105                 110

Ala Leu Val Ser Thr Gly Trp Asp Pro Gly Met Phe Ser Ile Asn Arg
        115                 120                 125

Val Tyr Ala Ala Ala Val Leu Ala Glu His Gln Gln His Thr Phe Trp
    130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
                165                 170                 175

Glu Lys Ala Arg Arg Gly Glu Ala Gly Asp Leu Thr Gly Lys Gln Thr
            180                 185                 190

His Lys Arg Gln Cys Phe Val Val Ala Asp Ala Asp His Glu Arg
        195                 200                 205

Ile Glu Asn Asp Ile Arg Thr Met Pro Asp Tyr Phe Val Gly Tyr Glu
    210                 215                 220

```
Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
            245                 250                 255

Phe Asn His Thr Val Glu Tyr Ile Leu Lys Leu Asp Arg Asn Pro Asp
            260                 265                 270

Phe Thr Ala Ser Ser Gln Ile Ala Phe Gly Arg Ala Ala His Arg Met
        275                 280                 285

Lys Gln Gln Gly Gln Ser Gly Ala Phe Thr Val Leu Glu Val Ala Pro
        290                 295                 300

Tyr Leu Leu Ser Pro Glu Asn Leu Asp Asp Leu Ile Ala Arg Asp Val
305                 310                 315                 320

<210> SEQ ID NO 5
<211> LENGTH: 297
<212> TYPE: PRT
<213> ORGANISM: Streptococcus thermophilus

<400> SEQUENCE: 5

Met Asp Lys Leu Arg Val Ala Val Val Gly Tyr Gly Asn Val Gly Arg
1               5                   10                  15

Tyr Ala Leu Glu Ala Val Gln Ala Ala Pro Asp Met Glu Leu Val Gly
            20                  25                  30

Val Val Arg Arg Lys Val Leu Ala Ala Thr Pro Glu Leu Thr Gly
            35                  40                  45

Val Arg Val Val Thr Asp Ile Ser Gln Leu Glu Gly Val Gln Gly Ala
        50                  55                  60

Leu Leu Cys Val Pro Thr Arg Ser Val Pro Glu Tyr Ala Glu Ala Met
65                  70                  75                  80

Leu Arg Arg Gly Ile His Thr Val Asp Ser Tyr Asp Ile His Gly Asp
            85                  90                  95

Leu Ala Asp Leu Arg Arg Arg Leu Asp Pro Val Ala Arg Glu His Gly
            100                 105                 110

Ala Ala Ala Val Ile Ser Ala Gly Trp Asp Pro Gly Thr Asp Ser Ile
        115                 120                 125

Ile Arg Ala Leu Leu Glu Phe Met Ala Pro Lys Gly Ile Thr Tyr Thr
130                 135                 140

Asn Phe Gly Pro Gly Met Ser Met Gly His Ser Val Ala Val Lys Ala
145                 150                 155                 160

Ile Pro Gly Val Arg Asp Ala Leu Ser Met Thr Ile Pro Ala Gly Met
            165                 170                 175

Gly Val His Lys Arg Ala Val Tyr Val Glu Leu Glu Pro Gly Ala Asp
            180                 185                 190

Phe Ala Glu Val Glu Arg Ala Ile Lys Thr Asp Pro Tyr Phe Val Arg
        195                 200                 205

Asp Glu Thr Arg Val Thr Gln Val Glu Ser Val Ser Ala Leu Met Asp
210                 215                 220

Val Gly His Gly Val Val Met Glu Arg Lys Gly Val Ser Gly Ala Thr
225                 230                 235                 240

His Asn Gln Leu Phe Arg Phe Glu Met Arg Ile Asn Asn Pro Ala Leu
            245                 250                 255

Thr Ala Gln Val Met Val Ala Ala Leu Arg Ala Ala Ala Arg Pro Gly
            260                 265                 270
```

-continued

```
Cys Tyr Thr Met Ile Glu Ile Pro Val Ile Asp Tyr Leu Pro Gly Asp
            275                 280                 285

Arg Glu Ala Trp Ile Arg Lys Leu Val
        290                 295

<210> SEQ ID NO 6
<211> LENGTH: 326
<212> TYPE: PRT
<213> ORGANISM: Ureibacillus thermosphaericus

<400> SEQUENCE: 6

Met Ser Lys Ile Arg Ile Gly Ile Val Gly Tyr Gly Asn Leu Gly Arg
1               5                   10                  15

Gly Val Glu Ala Ala Ile Gln Gln Asn Pro Asp Met Glu Leu Val Ala
            20                  25                  30

Val Phe Thr Arg Arg Asp Pro Lys Thr Val Ala Val Lys Ser Asn Val
        35                  40                  45

Lys Val Leu His Val Asp Asp Ala Gln Ser Tyr Lys Asp Glu Ile Asp
    50                  55                  60

Val Met Ile Leu Cys Gly Gly Ser Ala Thr Asp Leu Pro Glu Gln Gly
65                  70                  75                  80

Pro Tyr Phe Ala Gln Tyr Phe Asn Thr Ile Asp Ser Phe Asp Thr His
                85                  90                  95

Ala Arg Ile Pro Asp Tyr Phe Asp Ala Val Asn Ala Ala Glu Gln
            100                 105                 110

Ser Gly Lys Val Ala Ile Ile Ser Val Gly Trp Asp Pro Gly Leu Phe
        115                 120                 125

Ser Leu Asn Arg Leu Leu Gly Glu Val Val Leu Pro Val Gly Asn Thr
    130                 135                 140

Tyr Thr Phe Trp Gly Lys Gly Val Ser Gln Gly His Ser Asp Ala Ile
145                 150                 155                 160

Arg Arg Ile Gln Gly Val Lys Asn Ala Val Gln Tyr Thr Ile Pro Ile
                165                 170                 175

Asp Glu Ala Val Asn Arg Val Arg Ser Gly Glu Asn Pro Glu Leu Ser
            180                 185                 190

Thr Arg Glu Lys His Ala Arg Glu Cys Phe Val Val Leu Glu Glu Gly
        195                 200                 205

Ala Asp Pro Ala Lys Val Glu His Glu Ile Lys Thr Met Pro Asn Tyr
    210                 215                 220

Phe Asp Glu Tyr Asp Thr Thr Val His Phe Ile Ser Glu Glu Leu
225                 230                 235                 240

Lys Gln Asn His Ser Gly Met Pro His Gly Gly Phe Val Ile Arg Ser
                245                 250                 255

Gly Lys Ser Asp Glu Gly His Lys Gln Ile Ile Glu Phe Ser Leu Asn
            260                 265                 270

Leu Glu Ser Asn Pro Met Phe Thr Ser Ser Ala Leu Val Ala Tyr Ala
        275                 280                 285

Arg Ala Ala Tyr Arg Leu Ser Gln Asn Gly Asp Lys Gly Ala Lys Thr
    290                 295                 300

Val Phe Asp Ile Pro Phe Gly Leu Leu Ser Lys Ser Pro Glu Asp
305                 310                 315                 320

Leu Arg Lys Glu Leu Leu
                325
```

<210> SEQ ID NO 7
<211> LENGTH: 906
<212> TYPE: DNA
<213> ORGANISM: Thermosyntropha lipolytica

<400> SEQUENCE: 7

```
atgggtgaga  agattcgcgt  ggcaattgtt  ggctacggca  atatcggccg  ctacgcttta     60
gatgccatta  aagccgcccc  ggatatggaa  ctggccggtg  ttgtgcgtcg  tagcagctct    120
ttaggcgata  aaccggcaga  actggccgat  gtgccggtgg  tgggcagcat  caaagagctg    180
accggtgtga  aagtggcttt  attatgtaca  ccgacccgca  gtgtgccgga  gtatgcccgt    240
gaaattctgg  ctttaggcat  aataccgtga  tatagctatt  ctattcacgg  ccagctggca    300
gatttacgtt  tagaactgga  taaagtggcc  aaggagcaca  tgcagtggcc  gtgattagc     360
gctggttggg  atccgggtac  cgatagcatg  gtgcgttgca  tgttcgagtt  tatggccccg    420
aaaggcatta  cctacaccaa  tttcggcccg  gtatgtctt   taggtcatag  tggtgccgtg    480
aaagccgtga  aggcgtgaa   gaacgcttta  agcatgatta  tcccgctggg  taccggcgtt    540
caccgcatga  tggtgtatgt  ggaactggaa  ccgggtgccg  attttgccca  agttgaaaaa    600
gccgtgaaga  ccgatccgta  cttcgtgaag  gacgagaccc  acgtgattca  agttgaggat    660
gtggatgctt  taatcgatat  gggtaacggc  gtgctgatgg  aacgtaaagg  cgtgagcggc    720
ggcaccccata  accagctgct  gagctttagc  atgcgcatca  caacccccgc  tctgaccgcc    780
cagattatgg  tggccagtgc  ccgtgccagc  gtgaaacaga  accgggtgc   ctacaccatg    840
atccagatcc  cgatcattga  ctatatgtat  ggcgatccgg  atgaaatcat  ccgccaactg    900
gtttaa                                                                     906
```

<210> SEQ ID NO 8
<211> LENGTH: 301
<212> TYPE: PRT
<213> ORGANISM: Thermosyntropha lipolytica

<400> SEQUENCE: 8

Met Gly Glu Lys Ile Arg Val Ala Ile Val Gly Tyr Gly Asn Ile Gly
1               5                   10                  15

Arg Tyr Ala Leu Asp Ala Ile Lys Ala Ala Pro Asp Met Glu Leu Ala
            20                  25                  30

Gly Val Val Arg Arg Ser Ser Leu Gly Asp Lys Pro Ala Glu Leu
        35                  40                  45

Ala Asp Val Pro Val Val Gly Ser Ile Lys Glu Leu Thr Gly Val Lys
    50                  55                  60

Val Ala Leu Leu Cys Thr Pro Thr Arg Ser Val Pro Glu Tyr Ala Arg
65                  70                  75                  80

Glu Ile Leu Ala Leu Gly Ile Asn Thr Val Asp Ser Tyr Ser Ile His
                85                  90                  95

Gly Gln Leu Ala Asp Leu Arg Leu Glu Leu Asp Lys Val Ala Lys Glu
            100                 105                 110

His Asn Ala Val Ala Val Ile Ser Ala Gly Trp Asp Pro Gly Thr Asp
        115                 120                 125

Ser Met Val Arg Cys Met Phe Glu Phe Met Ala Pro Lys Gly Ile Thr
    130                 135                 140

Tyr Thr Asn Phe Gly Pro Gly Met Ser Leu Gly His Ser Gly Ala Val
145                 150                 155                 160

Lys Ala Val Lys Gly Val Lys Asn Ala Leu Ser Met Ile Ile Pro Leu
                165                 170                 175

```
Gly Thr Gly Val His Arg Met Met Val Tyr Val Glu Leu Glu Pro Gly
            180                 185                 190

Ala Asp Phe Ala Gln Val Glu Lys Ala Val Lys Thr Asp Pro Tyr Phe
        195                 200                 205

Val Lys Asp Glu Thr His Val Ile Gln Val Glu Asp Val Asp Ala Leu
    210                 215                 220

Ile Asp Met Gly Asn Gly Val Leu Met Glu Arg Lys Gly Val Ser Gly
225                 230                 235                 240

Gly Thr His Asn Gln Leu Leu Ser Phe Ser Met Arg Ile Asn Asn Pro
            245                 250                 255

Ala Leu Thr Ala Gln Ile Met Val Ala Ser Ala Arg Ala Ser Val Lys
        260                 265                 270

Gln Lys Pro Gly Ala Tyr Thr Met Ile Gln Ile Pro Ile Ile Asp Tyr
    275                 280                 285

Met Tyr Gly Asp Pro Asp Glu Ile Ile Arg Gln Leu Val
290                 295                 300

<210> SEQ ID NO 9
<211> LENGTH: 30
<212> TYPE: DNA
<213> ORGANISM: artificial
<220> FEATURE:
<223> OTHER INFORMATION: primer

<400> SEQUENCE: 9
caccatgggt gagaagattc gcgtggcaat                                      30

<210> SEQ ID NO 10
<211> LENGTH: 30
<212> TYPE: DNA
<213> ORGANISM: artificial
<220> FEATURE:
<223> OTHER INFORMATION: primer

<400> SEQUENCE: 10
ttaaaccagt tggcggatga tttcatccgg                                      30

<210> SEQ ID NO 11
<211> LENGTH: 30
<212> TYPE: DNA
<213> ORGANISM: artificial
<220> FEATURE:
<223> OTHER INFORMATION: primer

<400> SEQUENCE: 11
ccgtggatag ctatgatatt cacggccagc                                      30

<210> SEQ ID NO 12
<211> LENGTH: 30
<212> TYPE: DNA
<213> ORGANISM: artificial
<220> FEATURE:
<223> OTHER INFORMATION: primer

<400> SEQUENCE: 12
gctggccgtg aatatcatag ctatccacgg                                      30

<210> SEQ ID NO 13
<211> LENGTH: 906
<212> TYPE: DNA
<213> ORGANISM: Thermosyntropha lipolytica
```

<400> SEQUENCE: 13

```
atgggtgaga agattcgcgt ggcaattgtt ggctacggca atatcggccg ctacgcttta      60
gatgccatta aagccgcccc ggatatggaa ctggccggtg ttgtgcgtcg tagcagctct     120
ttaggcgata aaccggcaga actggccgat gtgccggtgg tgggcagcat caaagagctg     180
accggtgtga agtggctttt attatgtaca ccgacccgca gtgtgccgga gtatgcccgt     240
gaaattctgg cttttaggcat taataccgtg gatagctatg atattcacgg ccagctggca    300
gatttacgtt tagaactgga taaagtggcc aaggagcaca atgcagtggc cgtgattagc     360
gctggttggg atccgggtac cgatagcatg gtgcgttgca tgttcgagtt tatggccccg     420
aaaggcatta cctacaccaa tttcggcccg ggtatgtctt aggtcatag tggtgccgtg     480
aaagccgtga aggcgtgaa gaacgcttta agcatgatta tcccgctggg taccggcgtt     540
caccgcatga tggtgtatgt ggaactggaa ccgggtgccg attttgccca agttgaaaaa     600
gccgtgaaga ccgatccgta cttcgtgaag gacgagaccc acgtgattca agttgaggat     660
gtggatgctt taatcgatat gggtaacggc gtgctgatgg aacgtaaagg cgtgagcggc     720
ggcacccata accagctgct gagctttagc atgcgcatca acaaccccgc tctgaccgcc     780
cagattatgg tggccagtgc ccgtgccagc gtgaaacaga accgggtgc ctacaccatg      840
atccagatcc cgatcattga ctatatgtat ggcgatccgg atgaaatcat ccgccaactg     900
gtttaa                                                                906
```

<210> SEQ ID NO 14
<211> LENGTH: 301
<212> TYPE: PRT
<213> ORGANISM: Thermosyntropha lipolytica

<400> SEQUENCE: 14

```
Met Gly Glu Lys Ile Arg Val Ala Ile Val Gly Tyr Gly Asn Ile Gly
1               5                   10                  15

Arg Tyr Ala Leu Asp Ala Ile Lys Ala Ala Pro Asp Met Glu Leu Ala
            20                  25                  30

Gly Val Val Arg Arg Ser Ser Leu Gly Asp Lys Pro Ala Glu Leu
        35                  40                  45

Ala Asp Val Pro Val Val Gly Ser Ile Lys Glu Leu Thr Gly Val Lys
    50                  55                  60

Val Ala Leu Leu Cys Thr Pro Thr Arg Ser Val Pro Glu Tyr Ala Arg
65                  70                  75                  80

Glu Ile Leu Ala Leu Gly Ile Asn Thr Val Asp Ser Tyr Asp Ile His
                85                  90                  95

Gly Gln Leu Ala Asp Leu Arg Leu Glu Leu Asp Lys Val Ala Lys Glu
            100                 105                 110

His Asn Ala Val Ala Val Ile Ser Ala Gly Trp Asp Pro Gly Thr Asp
        115                 120                 125

Ser Met Val Arg Cys Met Phe Glu Phe Met Ala Pro Lys Gly Ile Thr
    130                 135                 140

Tyr Thr Asn Phe Gly Pro Gly Met Ser Leu Gly His Ser Gly Ala Val
145                 150                 155                 160

Lys Ala Val Lys Gly Val Lys Asn Ala Leu Ser Met Ile Ile Pro Leu
                165                 170                 175

Gly Thr Gly Val His Arg Met Met Val Tyr Val Glu Leu Glu Pro Gly
            180                 185                 190
```

```
Ala Asp Phe Ala Gln Val Glu Lys Ala Val Lys Thr Asp Pro Tyr Phe
    195                 200                 205

Val Lys Asp Glu Thr His Val Ile Gln Val Glu Asp Val Asp Ala Leu
    210                 215                 220

Ile Asp Met Gly Asn Gly Val Leu Met Glu Arg Lys Gly Val Ser Gly
225                 230                 235                 240

Gly Thr His Asn Gln Leu Leu Ser Phe Ser Met Arg Ile Asn Asn Pro
                245                 250                 255

Ala Leu Thr Ala Gln Ile Met Val Ala Ser Ala Arg Ala Ser Val Lys
                260                 265                 270

Gln Lys Pro Gly Ala Tyr Thr Met Ile Gln Ile Pro Ile Ile Asp Tyr
        275                 280                 285

Met Tyr Gly Asp Pro Asp Glu Ile Ile Arg Gln Leu Val
    290                 295                 300
```